United States Patent
Bellemin-Laponnaz et al.

(10) Patent No.: US 9,040,513 B2
(45) Date of Patent: May 26, 2015

(54) PROCESS FOR PREPARING PLATINUM-CARBENE COMPLEXES

(75) Inventors: Stéphane Bellemin-Laponnaz, Strasbourg (FR); Gilles Guichard, Gradignan (FR); Edith Chardon, Strasbourg (FR)

(73) Assignees: CENTRE NATIONAL DE LA RECHERCHE SCIENTIFIQUE, Paris (FR); UNIVRSITE DE STRASBOURG, STRASBOURG (FR)

( * ) Notice: Subject to any disclaimer, the term of this patent is extended or adjusted under 35 U.S.C. 154(b) by 1 day.

(21) Appl. No.: 13/996,206

(22) PCT Filed: Dec. 22, 2011

(86) PCT No.: PCT/FR2011/053155
§ 371 (c)(1),
(2), (4) Date: Nov. 12, 2013

(87) PCT Pub. No.: WO2012/085479
PCT Pub. Date: Jun. 28, 2012

(65) Prior Publication Data
US 2014/0058061 A1 Feb. 27, 2014

(30) Foreign Application Priority Data
Dec. 23, 2010 (FR) ..................... 10 61228

(51) Int. Cl.
*A61K 31/555* (2006.01)
*C07F 15/00* (2006.01)
*C07J 1/00* (2006.01)
*C07K 7/64* (2006.01)

(52) U.S. Cl.
CPC ........... *C07F 15/0086* (2013.01); *A61K 31/555* (2013.01); *C07J 1/007* (2013.01); *C07K 7/64* (2013.01)

(58) Field of Classification Search
None
See application file for complete search history.

(56) References Cited

U.S. PATENT DOCUMENTS
2011/0172199 A1 7/2011 Mailliet et al.

FOREIGN PATENT DOCUMENTS
WO 2009118475 A2 10/2009

OTHER PUBLICATIONS

Skander et al., "N-Heterocyclic Carbene-Amine (Pt(II) Complexes, a New Chemical Space for the Development of Platinum-Based Anti-cancer Drugs", Journal of Medicinal Chemistry, 2010, vol. 53, pp. 2146-2154, XP-002647109.
Barnard et al., "Mitochondrial permeability transition induced by dinuclear gold(I)-carbene complexes: potential new antimitochondrial antitumor agents", Journal of Inorganic Biochemistry, 2004, vol. 98, pp. 1642-1647.
Ray et al., "Anticancer and Antimicrobial Metallopharmaceutical Agents Based on Palladium, Gold, and Silver N-Heterocyclic Carbene Complexes", J. Am. Chem. Soc., 2007, vol. 129, pp. 15042-15053.
Teyssot et al., "Toxicity of Copper (I)-NHC Complexes Against Human Tumor Cells: Induction of Cell Cycle Arrest, Apoptosis, and DNA Cleavage", Chemistry European Journal, 2009, vol. 15, pp. 314-318.
International Search Report, dated Mar. 13, 2012, from corresponding PCT application.

*Primary Examiner* — Maury Audet
*Assistant Examiner* — Fred Reynolds
(74) *Attorney, Agent, or Firm* — Young & Thompson

(57) ABSTRACT

Described is a process for preparing platinum-carbene complexes.

20 Claims, No Drawings

PROCESS FOR PREPARING PLATINUM-CARBENE COMPLEXES

The present invention relates to a process for preparing platinum-carbene complexes.

Certain derivatives of platinum are known anticancer agents. The best known among them, cisplatin, is one of the anticancer agents most frequently used throughout the world. However, the application of cisplatin in chemotherapy remains very restricted owing to limitations on its activity with respect to cancer cells. In fact, cisplatin is only active against a limited spectrum of cancer cells. Certain cancer cell lines display a natural resistance to cisplatin, while certain other cancer cells can develop an acquired resistance.

Moreover, as a medicinal product cisplatin has several drawbacks, for example significant side-effects such as nephrotoxicity, neurotoxicity, or emetogenesis.

Moreover, the main method of administration of cisplatin is still intravenous administration, as cisplatin has low solubility in water (1 mg/ml).

Recently, a new family of metal complexes, the N-heterocyclic carbene complexes, has attracted the attention of scientists for their anticancer activity.

The carbene complexes of gold were investigated by Barnard et al. (Barnard, P. J. et al., *J. Inorg. Biochem.* 2004, 10, 1642). These complexes display antitumour activity.

Ray et al. described, in 2007 (*J. Am. Chem. Soc.* 2007, 129, 15042-15053), four carbene complexes of palladium, which have anticancer, antiproliferative or antibacterial properties.

In 2009, Teyssot et al. (*Chem. Eur. J.* 2009, 15, 314-318) showed that carbene complexes of copper display toxicity against human tumour cells, and are capable of inducing cessation of the cell cycle, apoptosis, or cleavage of DNA.

Skander et al. (*J. Med. Chem.* 2010, 53, 2146-2154) are developing a synthesis method for platinum-carbene complexes consisting of a three-step method, using a xylene solution of $Pt_2(dvtms)_3$ for obtaining complexes of (NHC)Pt(dvtms). However, this method, which requires the $Pt_2(dvtms)_3$ complex, is relatively expensive, and does not allow a platinum-carbene complex to be obtained with a satisfactory yield. Moreover, with this method it is only possible to synthesize a very limited number of complexes.

The subject of the present invention is to provide a novel process for preparing a family of platinum-carbene complexes.

One of the purposes of the invention is to offer a novel preparation method by which carbene compounds of platinum can be obtained that are stable and non-degradable.

Another aspect of the invention is to provide novel compounds with ligands endowing them with a useful solubility for use as medicinal products.

The present invention relates to a process for preparing platinum-carbene complexes of the following formula II:

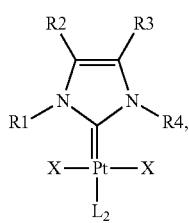

(Formula II)

in which:
R1 and R4 represent, independently of one another:
(i) a linear or branched C1-C12, in particular C1-C8 alkyl group, optionally substituted with an alkoxy group with 1 to 12 carbon atoms, in particular with 1 to 8 carbon atoms, with a $CF_3$ group or in particular with a trimethylsilyl group,
(ii) a linear or branched C2-C12, in particular C2-C8 alkenyl group, optionally substituted with an alkyl group with 1 to 12 carbon atoms, with an alkoxy group with 1 to 12 carbon atoms, in particular with 1 to 8 carbon atoms, with a $CF_3$ group or in particular with a trimethylsilyl group,
(iii) a linear or branched C2-C12, in particular C2-C8 alkynyl group, optionally substituted with an alkyl group with 1 to 12 carbon atoms, with an alkoxy group with 1 to 12 carbon atoms, in particular with 1 to 8 carbon atoms, with a $CF_3$ group or in particular with a trimethylsilyl group,
(iv) an aryl group having 1, 2 or 3 aromatic rings, in particular phenyl, or aralkyl with a C1-C12, in particular C1-C8 carbon chain, the aryl or aralkyl group being optionally substituted with a C1-C12, in particular C1-C8 alkyl group, or with a C1-C12, in particular C1-C8 alkoxy group, such as a methoxy, with a $CF_3$ group, or in particular with a trimethylsilyl group,
(v) a C3-C7 cycloalkyl, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl group, or
(vi) a polymer represented by the formula $-(CH_2CH_2O)_n-R'$ or a polymer represented by the formula $-(CH_2CH_2CH_2O)_n-R'$, in which n=1 to 40, in particular n=1 to 20, and R' is a C1-C12, in particular C1-C8 alkyl group, R2 and R3 represent, independently of one another:
a hydrogen,
an aryl or aralkyl group, in particular phenyl, benzyl, or
a linear or branched C2-C12, in particular C2-C8 alkynyl group, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl group, X represents iodine, bromine or chlorine,
$L_2$ represent:
(i) an amine of formula

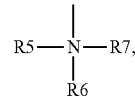

in which R5, R6 and R7 represent, independently of one another:
(a) a hydrogen,
(b) a linear or branched C1-C18 alkyl, optionally substituted with an estradiol,
(c) an aryl group having 1, 2 or 3 aromatic rings, in particular phenyl, or aralkyl with a C1-C12, in particular C1-C8 carbon chain, the aryl or aralkyl group being optionally substituted with a C1-C12, in particular C1-C8 alkoxy group, such as a methoxy, or an alkyl group with 1 to 12 carbon atoms, in particular with 1 to 8 carbon atoms, with a $CF_3$ group or with a trimethylsilyl group, (d) a C3-C7 cycloalkyl, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl, (e) a polymer represented by the formula $-(CH_2CH_2O)_n-R'$ or the formula $-(CH_2CH_2CH_2O)_n-R'$, in which n=1 to 40, in particular n=1 to 20, and R' is a C1-C12, in particular C1-C8 alkyl group, optionally substituted with an estradiol, (ii) a diamine of general formula $NH_2-(CH_2)_n-NH_2$, n=1 to 12 carbon atoms, (iii) a triamine of general formula $NH_2-(CH_2)_n-NH-(CH_2)_m-NH_2$, n=1 to 12 carbon atoms, m=1 to 12 carbon atoms, (iv) a linear or branched amino alcohol with 2 to 20 carbon atoms, in particular prolinol, (v) a linear or branched amino ester with 2 to 20 carbon atoms, in particular with 2 to 10 carbon atoms, (vi) a linear or branched amino amide with 2 to 20 carbon atoms, in particular pro linamide (vii) an amino acid in particular selected from the 20 proteinogenic α-amino acids or their esters or amides, and in particular selected from alanine or its esters or amides, arginine or its esters or amides, asparagine or its esters or amides, aspartate or its esters or amides, cysteine or its esters or amides, glutamate or its esters or amides, glutamine or its esters or amides, glycine or its esters or amides, isoleucine or its esters or amides, leucine or its esters or amides, lysine or its esters or amides, methionine or its esters or amides, serine or its esters or amides, threonine or its esters or amides, valine or its esters or amides, (viii) a beta or gamma amino acid or its esters or amides, (ix) a peptide, optionally cyclic, comprising 2 to 30, in particular 2 to 10 and in particular 2 to 3, amino acids, where the C-terminal acid and the N-terminal amine of said peptide and the side chains of said amino acids can be substituted with one or more substituent(s) selected independently from:
  a linear or branched C1-C6 alkyl,
  an aryl group having 1, 2 or 3 aromatic rings, in particular phenyl, or aralkyl with a C1-C12, in particular C1-C8 carbon chain,
  a C3-C7 cycloalkyl, optionally substituted with an alkyl group with 1 to 12 carbon atoms, in particular with 1 to 8 carbon atoms,
  an ad hoc protective group, (x) a morpholine, (xi) a piperazine optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl, (xii) a piperazine N-substituted with a dansyl or dabsyl group (xiii) a hydrazine monosubstituted with an aryl having 1, 2 or 3 aromatic rings, in particular a phenyl, or a linear or branched alkyl with 1 to 12 carbon atoms, (xiv) a glucamine optionally N-substituted with an alkyl group with 1 to 20 carbon atoms, in particular N-methylglucamine, N-ethylglucamine or N-dodecylglucamine, (xv) a glucosamine optionally N-substituted with an alkyl group with 1 to 20 carbon atoms, (xvi) a pseudopeptide of general formula $H-(NH-CH(R)-CH_2-X-CO)_n-NHR''$, with R being a side chain of one of the 20 proteinogenic amino acids; X being independently, throughout the sequence, $CH_2$, O or NH; n=1-15; R''=H, or a short alkyl or aralkyl chain, (xvii) a pseudopeptide of general formula $R_a-CO-CH(R_b)-NH-CO-NH-CH(R_c)-CO-R_d$ in which $R_a$ and $R_d$ represent, independently of one another, H, a linear or branched C1-C6 alkyl group, a C3-C7 monocyclic cycloalkyl group, or a carboxylic acid protective group; $R_b$ represents the side chain of lysine, the amine of said side chain being optionally substituted with a $-CO-(CH_2)_5-NH_2$ group; $R_c$ represents a side chain of one of the 20 proteinogenic amino acids, optionally protected by an ad hoc protective group, (xvii) a polymer represented by the general formula $NH_2-(CH_2(CH_2)_iNH)_{(n-1)}-H$, in which i=1, 2 or 3, n=1 to 1000, in particular n=1 to 500, more particularly from 1 to 100, said polymer forming moreover m-1 coordination bonds with m-1 groups of formula 1:

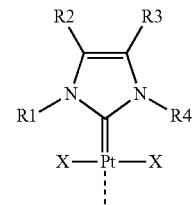

where $R_1$, $R_2$, $R_3$, $R_4$ and X are as defined above, the number m being comprised between 1 and n, the ratio m/n representing the number of platinum atoms to the number of amines of $-NH-$ or $-NH_2$ type, in particular being comprised between 1/50 and 1/2, more particularly between 1/20 and 1/2, in particular the preparation of a compound of the following formula IIa:

Formula IIa

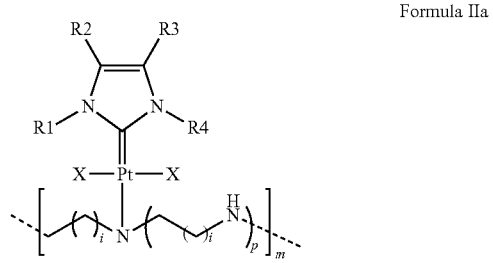

in which
R1 and R4 represent, independently of one another:
(i) a linear or branched C1-C12, in particular C1-C8 alkyl group, optionally substituted with an alkoxy group with 1 to 12 carbon atoms, in particular with 1 to 8 carbon atoms, with a $CF_3$ group or in particular with a trimethylsilyl group,
(ii) a linear or branched C2-C12, in particular C2-C8 alkenyl group, optionally substituted with an alkyl group with 1 to 12 carbon atoms, with an alkoxy group with 1 to 12 carbon atoms, in particular with 1 to 8 carbon atoms, with a $CF_3$ group, or in particular with a trimethylsilyl group, (iii) a linear or branched C2-C12, in particular C2-C8 alkynyl group, optionally substituted with an alkyl group with 1 to 12 carbon atoms, with an alkoxy group with 1 to 12 carbon atoms, in particular with 1 to 8 carbon atoms, with a $CF_3$ group, or in particular with a trimethylsilyl group, (iv) an aryl group having 1, 2 or 3 aromatic rings, in particular phenyl, or aralkyl with a C1-C12, in particular C1-C8 carbon chain, the aryl or aralkyl group being optionally substituted with a C1-C12, in particular C1-C8 alkyl group, or with a C1-C12, in particular C1-C8 alkoxy group, such as a methoxy, with a $CF_3$ group, or in particular with a trimethylsilyl group, (v) a C3-C7 cycloalkyl, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl group, or (vi) a polymer represented by the formula $—(CH_2CH_2O)_n—R'$ or a polymer represented by the formula $—(CH_2CH_2CH_2O)_n—R'$, in which n=1 to 40, in particular n=1 to 20, and R' is a C1-C12, in particular C1-C8 alkyl group, and R2 and R3 represent, independently of one another:

a hydrogen, an aryl or aralkyl group, in particular phenyl, benzyl, or a linear or branched C2-C12, in particular C2-C8 alkynyl group, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl group, X represents iodine, bromine or chlorine, m=1 to 1000, in particular m=1 to 100, more particularly from 1 to 50, p=0 to 50, in particular p=1 to 20, more particularly from 1 to 10, p representing the ratio of the number of platinum atoms to the number of amines of —NH— or —$NH_2$ type, i=1, 2 or 3, said process comprising reaction of the compound of formula I:

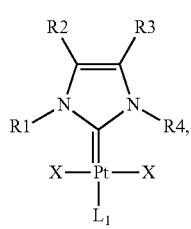

Formula I in which:

R1, R2, R3, R4 and X have the meanings given above, $L_1$ representing a pyridine, or a pyridine substituted with iodine, bromine or chlorine, in particular 3-bromopyridine, or 3-chloropyridine, or disubstituted with iodine, bromine or chlorine, in particular 3,5-dibromopyridine, with a ligand $L_2$, or a salt of a ligand $L_2$, said reaction being carried out optionally in the presence of a solvent.

Diagram I below illustrates the reaction between the compound of formula I and the ligand $L_2$, for obtaining a compound of formula II.

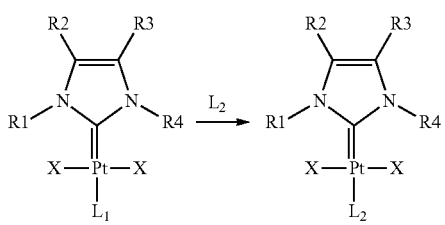

DIAGRAM I

The invention is based on the unexpected experimental results obtained by the inventors: under certain experimental conditions, the platinum-carbene complexes of formula I, bearing a pyridine or a pyridine substituted with a halogen as ligand, are capable of reacting with nitrogenous compounds, which can be complex molecules, and of replacing their ligand with these nitrogenous compounds.

The inventors found, surprisingly, that the choice of ligand $L_2$ is decisive for accomplishment of the reaction described in diagram 1. In fact, contacting a compound of formula I with any ligand at all does not always allow access to the compounds of formula II. As an example, when the compound of formula I reacts with thiophene or benzyl azide as $L_2$ under experimental conditions such as those used in the invention, no reactivity is observed. As another example, reaction between the compound of formula I and 1-decanethiol as ligand $L_2$ only results in products that are unstable and degradable.

By "ester" of an amino acid is meant: the acid function of the α-amino acid is protected in the form of esters of linear or branched alkyl or of alkenyl (allyls) with 1 to 20 carbon atoms or in the form of benzyl esters, unsubstituted, or substituted with methoxy groups or with an $NO_2$ group.

By "amide" of an amino acid is meant: the acid function of the α-amino acid is protected in the form of amide, we have $NH_2—CH(R)—CONH_2$, R being a linear or branched alkyl with 1 to 20 carbon atoms.

By "short alkyl or aralkyl chain" is meant a C1-C8, in particular C1-C6 carbon chain, said chain in particular being linear or branched.

By "ad hoc protective group" is meant a group intended to protect a function, for example a carboxylic acid protective group, against undesirable reactions during the synthesis steps. The protective groups commonly used are described in Greene, "Protective Groups in Organic Synthesis" (John Wiley & Sons, New York (1981).

The bond between Pt and the ligand $L_1$ or ligand $L_2$ represented by a solid line does not correspond to a covalent bond, but to a coordination bond.

The coordination bond between Pt of the m-1 groups of formula I and m-1 amines of —NH— or —$NH_2$ type of the polymer of general formula $NH_2—(CH_2(CH_2)_iNH)_{(n-1)}—H$ is represented by a dotted line.

In the context of the invention, the peptide or pseudopeptide as ligand of the compound of formula II can be selected from the peptides known to a person skilled in the art.

As an example of ligand L, there can be mentioned the cyclized cyclic peptide H-Arg(HCl)-Gly-Asp($CH_2CCl_3$)-D-Phe-Lys($N_3$)—OH (J. Org. Chem. 2003, 68, 4464-4471).

As another example of ligand L, there can be mentioned the pseudopeptide N—[N—[(S)-1,3-dicarboxypropyl]carbamoyl]-(S)-lysine (DCL), a ligand known from the prostate specific membrane antigen (PSMA) (*J. Med. Chem.* 2009, 52, 347-357) or a derivative thereof such as MeO-L-Lys-CO-L-Glu(OMe)-OMe, MeO-L-Lys(CO—(CH$_2$)$_5$—NH$_2$)—CO-L-Glu(OMe)-OMe or CCl$_3$—CH$_2$—O-L-Lys-CO-L-Glu(O—CH$_2$—CCl$_3$)—OCH$_2$CCl$_3$.

If L$_2$ or its precursor, for example L$_2$ in the form of salt (which is generally the case with the derivatives of amino acids), is solid at the reaction temperature, then it is necessary to use a solvent for the reaction (i.e. ethanol, methanol, etc.).

In a particular embodiment, the process according to the invention is carried out in the presence of solvent, said solvent being selected from ethanol, methanol, dichloromethane, tetrahydrofuran, toluene, or ethyl acetate.

In another particular embodiment, the process according to the invention is carried out in the absence of solvent, L$_2$ being liquid at the reaction temperature and performing the role of solvent.

The process according to the invention can be carried out in the presence of a base.

In a particular embodiment, the process according to the invention comprises the addition of a base selected from a tertiary amine, in particular selected from triethylamine, or diisopropylethylamine, when the ligand L$_2$ is in the form of salt.

In a particular embodiment of the invention, the salt of the ligand L$_2$ is in the form of ammonium salt, in particular ammonium hydrochloride or ammonium trifluoroacetate.

However, when derivatives L$_2$ are available or marketed in the form of salts (this is the case with derivatives of amino acids), it is not necessary to add a base during implementation of the process according to the invention.

An advantageous embodiment of the invention relates to a process for preparing the platinum-carbene complexes of formula II, carried out at a temperature from 10° C. to 65° C.

In a more advantageous embodiment, the process according to the invention is carried out at a temperature from 10° C. to 35° C.

In another more advantageous embodiment, the process according to the invention is carried out at a temperature from 35° C. to 65° C.

A particularly advantageous embodiment of the invention relates to a process for preparing the platinum-carbene complexes of formula II, carried out in the presence of ethanol as solvent, at a temperature from 45° C. to 65° C., in particular at 55° C.

Ethanol can dissolve most of the derivatives L$_2$ and this means it is possible to carry out the reaction at 55° C.

Another particularly advantageous embodiment of the invention relates to a process for preparing the platinum-carbene complexes of formula II, carried out in the presence of dichloromethane as solvent, at a temperature from 10° C. to 35° C., in particular at 20° C.

Dichloromethane can dissolve the compounds of formula I and L2 and thus makes it possible to carry out the reactions at room temperature.

In a particular embodiment, the invention relates to a process for preparing the platinum-carbene complexes of formula II, in which the compound of formula I is obtained by reacting (i) a compound of formula III:

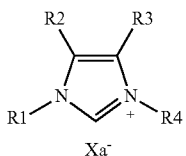

Formula III in which:
(a) R1, R2, R3, R4 have the meanings given above,
(b) Xa represents iodine, bromine or chlorine, or a counter-anion such as mesylate, tosylate, tetrafluoroborate, hexafluorophosphate, with the following molecules:
(ii) Pt(Xb)$_2$, in which Xb represents iodine, bromine or chlorine, and
(iii) a ligand L$_1$, L$_1$ representing a pyridine, a pyridine substituted with iodine, bromine or chlorine, in particular 3-bromopyridine, or 3-chloropyridine, or disubstituted with iodine, bromine or chlorine, in particular 3,5-dibromopyridine, and
(iv) optionally NaXc in excess relative to PtXb$_2$ or to Xa$^-$, Xc representing iodine, bromine or chlorine,
said reaction being carried out optionally in the presence of a solvent, in particular toluene.

Diagram II below illustrates the reaction between the compound of formula III, Pt(Xb)$_2$ and the ligand L$_1$, for obtaining the compound of formula I.

DIAGRAM II

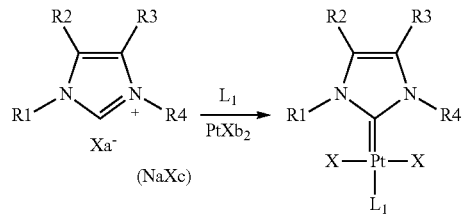

By "NaXc in excess" is meant that the number of moles of Xc is in excess both relative to the number of moles of Xa and relative to the number of moles of Xb.

When Xa is different from Xb, NaXc is added in excess relative to Xa and to Xb.

When NaXc is added in excess, Xc can be identical to or different from Xa or Xb, and in this case, X in formula I corresponds to Xc.

When Xa is identical to Xb, the addition of NaXc is not necessary. In this case, in formula I, X corresponds to Xa and to Xb.

The compound of formula III is commercially available, or is obtained according to syntheses fully described in the literature (review: Chardon et al., Chem. Rev. 2011, at press).

PtCl$_2$, PtBr$_2$ or PtI$_2$ are commercially available.

In a particular embodiment of the invention, the reaction between the compound of formula III, Pt(Xb)$_2$ and the ligand L$_1$ is carried out in the presence of NaXc in excess with respect to Xa and Xb, when Xa is different from Xb.

In another particular embodiment of the invention, the reaction between the compound of formula III, Pt(Xb)$_2$ and the ligand L$_1$ is carried out without the addition of NaXc, when Xa and Xb are identical.

In another particular embodiment of the invention, the reaction between the compound of formula III, Pt(Xb)$_2$ and the ligand L$_1$ is carried out in the presence of a base, in particular a base selected from sodium carbonate, potassium carbonate or caesium carbonate.

The presence of a base in the aforesaid reaction makes it possible to deprotonate the imidazolium and form the carbene ligand in situ.

In a particular embodiment of the invention, the reaction between the compound of formula III and the ligand L$_1$ is carried out in the presence of solvent.

The presence of solvent in the aforesaid reaction makes it possible to use L1 in an equimolar quantity, when L1 is expensive or when L1 is a solid at room temperature (example: pyridine disubstituted with halogens) and its excess is difficult to remove at the end of the reaction.

In another particular embodiment of the invention, the reaction between the compound of formula III and the ligand L$_1$ is carried out without the addition of solvent.

In fact, when L$_1$ is liquid at the reaction temperature, L$_1$ can perform a role of solvent.

In this instance, L1 is introduced in large excess, for example in quantities comparable to those of a solvent, in the reaction medium.

In a particular embodiment of the invention, the reaction between the compound of formula III, Pt(Xb)$_2$ and the ligand L$_1$ is carried out without solvent, ligand L$_1$ being liquid at the reaction temperature.

In this case, L1 is introduced in quantities comparable to those of a solvent.

In an advantageous embodiment of the invention, the reaction between the compound of formula III and the ligand L$_1$ is carried out in the absence of solvent at a temperature from 80° C. to 140° C., in particular from 90° C. to 130° C.

When L1 is introduced in quantities comparable to those of a solvent, the aforesaid reaction makes it possible to produce the compound of formula I with a better yield.

In another advantageous embodiment of the invention, the reaction between the compound of formula III and the ligand L$_1$ is carried out in the presence of toluene as solvent, at a temperature from 90° C. to 110° C., in particular at 100° C.

When L1 is expensive or when L1 is a solid at room temperature (example: pyridine disubstituted with halogens), the aforesaid reaction makes it possible to use L1 in an equimolar quantity.

In a particular embodiment, the invention relates to a process for preparing platinum-carbene complexes of the following formula II:

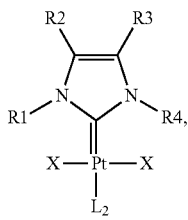

(Formula II)

in which:

R1 and R4 represent, independently of one another:
(i) a linear or branched C1-C12, in particular C1-C8 alkyl group, optionally substituted with an alkoxy group with 1 to 12 carbon atoms, in particular with 1 to 8 carbon atoms, with a CF$_3$ group or in particular with a trimethylsilyl group,
(ii) a linear or branched C2-C12, in particular C2-C8 alkenyl group, optionally substituted with an alkyl group with 1 to 12 carbon atoms, with an alkoxy group with 1 to 12 carbon atoms, in particular with 1 to 8 carbon atoms, with a CF$_3$ group, or in particular with a trimethylsilyl group,
(iii) a linear or branched C2-C12, in particular C2-C8 alkynyl group, optionally substituted with an alkyl group with 1 to 12 carbon atoms, with an alkoxy group with 1 to 12 carbon atoms, in particular with 1 to 8 carbon atoms, with a CF$_3$ group, or in particular with a trimethylsilyl group,
(iv) an aryl group having 1, 2 or 3 aromatic rings, in particular phenyl, or aralkyl with a C1-C12, in particular C1-C8 carbon chain, the aryl or aralkyl group being optionally substituted with a C1-C12, in particular C1-C8 alkyl group, or with a C1-C12, in particular C1-C8 alkoxy group, such as a methoxy, with a CF$_3$ group, or in particular with a trimethylsilyl group,
(v) a C3-C7 cycloalkyl, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a CF$_3$ group, or in particular with a trimethylsilyl group, or
(vi) a polymer represented by the formula —(CH$_2$CH$_2$O)$_n$—R' or a polymer represented by the formula —(CH$_2$CH$_2$CH$_2$O)$_n$—R', in which n=1 to 40, in particular n=1 to 20, and R' is a C1-C12, in particular C1-C8 alkyl group, R2 and R3 represent, independently of one another:
a hydrogen,
an aryl or aralkyl group, in particular phenyl, benzyl, or
a linear or branched C2-C12, in particular C2-C8 alkynyl group, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a CF$_3$ group, or in particular with a trimethylsilyl group, X represents iodine, bromine or chlorine, L$_2$ represent:
(i) an amine of formula

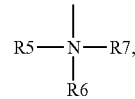

in which R5, R6 and R7 represent, independently of one another:
(a) a hydrogen,
(b) a linear or branched C1-C18 alkyl, optionally substituted with an estradiol,
(c) an aryl group having 1, 2 or 3 aromatic rings, in particular phenyl, or aralkyl with a C1-C12, in particular C1-C8 carbon chain, the aryl, aralkyl group being optionally substituted with a C1-C12, in particular C1-C8 alkoxy group, such as a methoxy, or an alkyl group with 1 to 12 carbon atoms, in particular with 1 to 8 carbon atoms, with a CF$_3$ group or with a trimethylsilyl group, (d) a C3-C7 cycloalkyl, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl, (e) a polymer represented by the formula $-(CH_2CH_2O)_n-R'$ or by the formula $-(CH_2CH_2CH_2O)_n-R'$, in which n=1 to 40, in particular n=1 to 20, and R' is a C1-C12, in particular C1-C8 alkyl group, optionally substituted with an estradiol, (ii) a diamine of general formula $NH_2-(CH_2)_n-NH_2$, n=1 to 12 carbon atoms, (iii) a triamine of general formula $NH_2-(CH_2)_n-NH-(CH_2)_m-NH_2$, n=1 to 12 carbon atoms, m=1 to 12 carbon atoms, (iv) a linear or branched amino alcohol with 2 to 20 carbon atoms, in particular prolinol, (v) a linear or branched amino ester with 2 to 20 carbon atoms, in particular with 2 to 10 carbon atoms, (vi) a linear or branched amino amide with 2 to 20 carbon atoms, in particular prolinamide, (vii) an amino acid in particular selected from the 20 proteinogenic α-amino acids or their esters or amides, and in particular selected from alanine or its esters or amides, arginine or its esters or amides, asparagine or its esters or amides, aspartate or its esters or amides, cysteine or its esters or amides, glutamate or its esters or amides, glutamine or its esters or amides, glycine or its esters or amides, isoleucine or its esters or amides, leucine or its esters or amides, lysine or its esters or amides, methionine or its esters or amides, serine or its esters or amides, threonine or its esters or amides, valine or its esters or amides, (viii) a beta or gamma amino acid or its esters or amides (ix) a peptide, optionally cyclic, comprising 2 to 30 amino acids, in particular from 2 to 10, (x) a morpholine, (xi) a piperazine optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, in particular with a trimethylsilyl group, (xii) a piperazine N-substituted with a dansyl or dabsyl group, (xiii) a hydrazine monosubstituted with an aryl having 1, 2 or 3 aromatic rings, in particular a phenyl, or a linear or branched alkyl with 1 to 12 carbon atoms, (xiv) a glucamine optionally N-substituted with an alkyl group with 1 to 20 carbon atoms, in particular N-methylglucamine, N-ethylglucamine or N-dodecylglucamine, (xv) a glucosamine optionally N-substituted with an alkyl group with 1 to 20 carbon atoms, or (xvi) a pseudopeptide of general formula $H-(NH-CH(R)-CH_2-X-CO)_n-NHR''$, with R being a side chain of one of the 20 proteinogenic amino acids; X being independently, throughout the sequence, $CH_2$, O or NH; n=1-15; R''=H, or a short alkyl or aralkyl chain, (xvii) a pseudopeptide of general formula $R_a-CO-CH(R_b)-NH-CO-NH-CH(R_c)-CO-R_d$ in which $R_a$ and $R_d$ represent, independently of one another, H, a linear or branched C1-C6 alkyl group, a C3-C7 monocyclic cycloalkyl group, or a carboxylic acid protective group; $R_b$ represents the side chain of lysine, the amine of said side chain being optionally substituted with a $-CO-(CH_2)_5-NH_2$ group; $R_c$ represents a side chain of one of the 20 proteinogenic amino acids, optionally protected by an ad hoc protective group, (xvii) a polymer represented by the general formula $NH_2-(CH_2(CH_2)_iNH)_{(n-1)}-H$, in which i=1, 2 or 3, n=1 to 1000, in particular n=1 to 500, more particularly from 1 to 100, said polymer forming moreover m-1 coordination bonds with m-1 groups of formula 1:

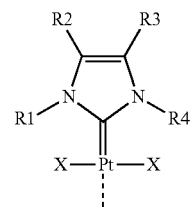

where $R_1$, $R_2$, $R_3$, $R_4$ and X are as defined above,
the number m being comprised between 1 and n, the ratio m/n representing the number of platinum atoms to the number of amines of $-NH-$ or $-NH_2$ type, in particular being comprised between 1/50 and 1/2, more particularly between 1/20 and 1/2, said process comprising:

(i) reacting a compound of the following formula III:

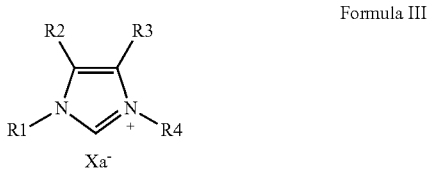

in which:
(a) R1, R2, R3, R4 have the meanings given above,
(b) Xa represents iodine, bromine or chlorine,
with $Pt(Xb)_2$, and a ligand L1 and optionally NaXc in excess, in order to obtain a compound of the following formula I

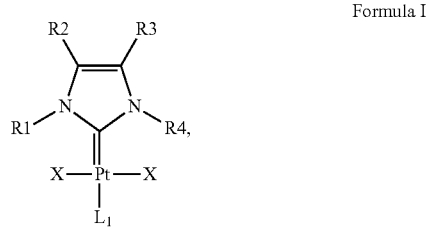

in which
R1, R2, R3, R4 and X have the meanings given above,
$L_1$ represents a pyridine, or a pyridine substituted with iodine, bromine or chlorine, in particular 3-bromopyridine, or 3-chloropyridine, or disubstituted with iodine, bromine or chlorine, in particular 3,5-dibromopyridine, and (ii) reacting the compound of formula I above with a ligand $L_2$, carried out optionally in the presence of a solvent, in order to obtain a platinum-carbene complex of formula II above.

The process according to the invention makes it possible to access novel platinum-carbene complexes.

In an advantageous embodiment, the process according to the invention makes it possible to obtain platinum-carbene complexes of the following formula II:

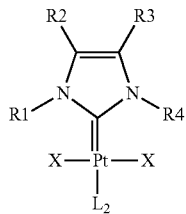

Formula II in which
(I) if:
R1 and R4 represent, independently of one another:
(i) a linear or branched C1-C12, in particular C1-C8 alkyl group, optionally substituted with an alkoxy group with 1 to 12 carbon atoms, in particular with 1 to 8 carbon atoms, with a $CF_3$ group or in particular with a trimethylsilyl group,
(ii) a linear or branched C2-C12, in particular C2-C8 alkenyl group, optionally substituted with an alkyl group with 1 to 12 carbon atoms, with an alkoxy group with 1 to 12 carbon atoms, in particular with 1 to 8 carbon atoms, with a $CF_3$ group, or in particular with a trimethylsilyl group,
(iii) a linear or branched C2-C12, in particular C2-C8 alkynyl group, optionally substituted with an alkyl group with 1 to 12 carbon atoms, with an alkoxy group with 1 to 12 carbon atoms, in particular with 1 to 8 carbon atoms, with a $CF_3$ group, or in particular with a trimethylsilyl group,
(iv) an aryl group having 1, 2 or 3 aromatic rings, in particular phenyl, or aralkyl with a C1-C12, in particular C1-C8 carbon chain, the aryl or aralkyl group being optionally substituted with a C1-C12, in particular C1-C8 alkyl group, or with a C1-C12, in particular C1-C8 alkoxy group, such as a methoxy, with a $CF_3$ group, or in particular with a trimethylsilyl group,
(v) a C3-C7 cycloalkyl, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl group, or
(vi) a polymer represented by the formula $—(CH_2CH_2O)_n—R'$ or a polymer represented by the formula $—(CH_2CH_2CH_2O)_n—R'$, in which n=1 to 40, in particular n=1 to 20, and R' is a C1-C12, in particular C1-C8 alkyl group, and R2 and R3 represent, independently of one another:
a hydrogen,
an aryl or aralkyl group, in particular phenyl, benzyl, or
a linear or branched C2-C12, in particular C2-C8 alkynyl group, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl group, then $L_2$ represents:
(i) an amine of formula

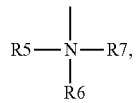

in which R5, R6 and R7 represent, independently of one another:
(a) a linear or branched, non-cyclized C1-C18 alkyl, optionally substituted with an estradiol,
(b) an aryl having 1 or 2 or 3 aromatic rings, in particular phenyl, optionally substituted with a C1-C12, in particular C1-C8 alkoxy group, such as a methoxy, or with an alkyl group with 1 to 12 carbon atoms, in particular with 1 to 8 carbon atoms, with a $CF_3$ group or in particular with a trimethylsilyl,
(c) a polymer represented by the formula $—(CH_2CH_2O)_n—R'$ or the formula $—(CH_2CH_2CH_2O)_n—R'$, in which n=1 to 40, in particular n=1 to 20, and R' is a C1-C12, in particular C1-C8 alkyl group, optionally substituted with an estradiol,
provided that at least one of the R5, R6 and R7 radicals is different from hydrogen,
(ii) a diamine of general formula $NH_2—(CH_2)_n—NH_2$, n=1 to 12 carbon atoms,
(iii) a triamine of general formula $NH_2—(CH_2)_n—NH—(CH_2)_m—NH_2$, n=1 to 12 carbon atoms, m=1 to 12 carbon atoms,
(iv) a linear or branched amino alcohol with 2 to 20 carbon atoms, in particular prolinol,
(v) a linear or branched amino ester with 2 to 20 carbon atoms, in particular with 2 to 10 carbon atoms,
(vi) a linear or branched amino amide with 2 to 20 carbon atoms, in particular prolinamide,
(vii) an amino acid in particular selected from the 20 proteinogenic α-amino acids or their esters or amides, and in particular selected from alanine or its esters or amides, arginine or its esters or amides, asparagine or its esters or amides, aspartate or its esters or amides, cysteine or its esters or amides, glutamate or its esters or amides, glutamine or its esters or amides, glycine or its esters or amides, isoleucine or its esters or amides, leucine or its esters or amides, lysine or its esters or amides, methionine or its esters or amides, serine or its esters or amides, threonine or its esters or amides, valine or its esters or amides,
(viii) a beta or gamma amino acid or its esters or amides,
(ix) a peptide, optionally cyclic, comprising 2 to 30 amino acids, in particular from 2 to 10,
(x) a hydrazine monosubstituted with an aryl having 1, 2 or 3 aromatic rings, in particular a phenyl, or a linear or branched alkyl with 1 to 12 carbon atoms,
(xi) a glucamine optionally N-substituted with an alkyl group with 1 to 20 carbon atoms, in particular N-methylglucamine, N-ethylglucamine or N-dodecylglucamine,
(xii) a glucosamine optionally N-substituted with an alkyl group with 1 to 20 carbon atoms,
(xiii) a pseudopeptide of general formula $H—(NH—CH(R)—CH_2—X—CO)_n—NHR''$, with R being a side chain of one of the 20 proteinogenic amino acids; X being independently, throughout the sequence, $CH_2$, O or NH; n=1-15; R''=H, or a short alkyl or aralkyl chain, (xiv) a pseudopeptide of general formula $R_a$—CO—CH($R_b$)—NH—CO—NH—CH($R_c$)—CO—$R_d$ in which $R_a$ and $R_d$ represent, independently of one another, H, a linear or branched C1-C6 alkyl group, a C3-C7 monocyclic cycloalkyl group, or a carboxylic acid protective group; $R_b$ represents the side chain of lysine, the amine of said side chain being optionally substituted with a —CO—(CH$_2$)$_5$—NH$_2$ group; $R_c$ represents a side chain of one of the 20 proteinogenic amino acids, optionally protected by an ad hoc protective group, or (xv) a polymer represented by the general formula NH$_2$—(CH$_2$(CH$_2$)$_i$NH)$_{(n-1)}$—H, in which i=1, 2 or 3, n=1 to 1000, in particular n=1 to 500, more particularly from 1 to 100, said polymer forming moreover m-1 coordination bonds with m-1 groups of formula 1:

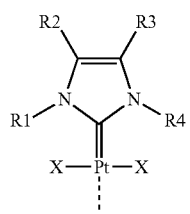

where $R_1$, $R_2$, $R_3$, $R_4$ and X are as defined above, the number m being comprised between 1 and n, the ratio m/n representing the number of platinum atoms to the number of amines of type —NH— or —NH$_2$, in particular being comprised between 1/50 and 1/2, more particularly between 1/20 and 1/2, and X represents iodine, bromine or chlorine;

(IIa) if:

R1 and R4 represent, independently of one another:

(i) a linear or branched C1-C12, in particular C1-C8 alkyl group, optionally substituted with an alkoxy group with 1 to 12 carbon atoms, in particular with 1 to 8 carbon atoms, with a CF$_3$ group or in particular with a trimethylsilyl group, (ii) a linear or branched C2-C12, in particular C2-C8 alkenyl group, optionally substituted with an alkyl group with 1 to 12 carbon atoms, with an alkoxy group with 1 to 12 carbon atoms, in particular with 1 to 8 carbon atoms, with a CF$_3$ group or in particular with a trimethylsilyl group, (iii) a linear or branched C2-C12, in particular C2-C8 alkynyl group, optionally substituted with an alkyl group with 1 to 12 carbon atoms, with an alkoxy group with 1 to 12 carbon atoms, in particular with 1 to 8 carbon atoms, with a CF$_3$ group or in particular with a trimethylsilyl group, (iv) an aryl group having 1, 2 or 3 aromatic rings, in particular phenyl, or aralkyl with a C1-C12, in particular C1-C8 carbon chain, the aryl or aralkyl group being optionally substituted with a C1-C12, in particular C1-C8 alkyl group, or with a C1-C12, in particular C1-C8 alkoxy group, such as a methoxy, with a CF$_3$ group, or in particular with a trimethylsilyl group, (v) a C3-C7 cycloalkyl, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a CF$_3$ group, or in particular with a trimethylsilyl group, or (vi) a polymer represented by the formula —(CH$_2$CH$_2$O)$_n$—R' or a polymer represented by the formula —(CH$_2$CH$_2$CH$_2$O)$_n$—R', in which n=1 to 40, in particular n=1 to 20, and R' is a C1-C12, or in particular C1-C8, alkyl group, with the condition that R1 or R4 represents:

a linear or branched C1-C6 alkyl group, substituted with a trimethylsilyl group, or a linear or branched, noncyclized C7-C12, in particular C7-C8 alkyl group, optionally substituted with an alkoxy group with 1 to 12 carbon atoms, in particular with 1 to 8 carbon atoms, with a CF$_3$ group or in particular with a trimethylsilyl group, a linear or branched C2-C12, in particular C2-C8 alkenyl group, substituted with a trimethylsilyl group, a linear or branched C2-C12, in particular C2-C8 alkynyl group, optionally substituted with an alkyl group with 1 to 12 carbon atoms, with an alkoxy group with 1 to 12 carbon atoms, in particular with 1 to 8 carbon atoms, with a CF$_3$ group or in particular with a trimethylsilyl group, a polymer represented by the formula —(CH$_2$CH$_2$O)$_n$—R' or a polymer represented by the formula —(CH$_2$CH$_2$CH$_2$O)$_n$—R', in which n=1 to 40, in particular n=1 to 20, and R' is a C1-C12, in particular C1-C8 alkyl group, and R2 and R3 represent, independently of one another:

a hydrogen, an aryl or aralkyl group, in particular phenyl, benzyl, or a linear or branched C2-C12, in particular C2-C8 alkynyl group, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a CF$_3$ group, or in particular with a trimethylsilyl group, II (b) or, if:

R2 and R3 represent, independently of one another:

a hydrogen, an aryl or aralkyl group, in particular phenyl, benzyl, or a linear or branched C2-C12, in particular C2-C8 alkynyl group, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a CF$_3$ group, or in particular with a trimethylsilyl group, with the condition that R2 or R3 represents:

an aralkyl group with a C1-C12, in particular C1-C8 carbon chain, the aralkyl group being optionally substituted with a C1-C12, in particular C1-C8 alkyl group, or with a C1-C12, in particular C1-C8 alkoxy group, such as a methoxy, with a CF$_3$ group, or in particular with a trimethylsilylbenzyl group, or a linear or branched C2-C12, in particular C2-C8 alkynyl, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a CF$_3$ group, or in particular with a trimethylsilyl group, and R1 and R4 represent, independently of one another:

(i) a linear or branched C1-C12, in particular C1-C8 alkyl group, optionally substituted with an alkoxy group with 1 to 12 carbon atoms, in particular with 1 to 8 carbon atoms, with a CF$_3$ group or in particular with a trimethylsilyl group, (ii) a linear or branched C2-C12, in particular C2-C8 alkenyl group, optionally substituted with an alkyl group with 1 to 12 carbon atoms, with an alkoxy group with 1 to 12 carbon atoms, in particular with 1 to 8 carbon atoms, with a $CF_3$ group or in particular with a trimethylsilyl group, (iii) a linear or branched C2-C12, in particular C2-C8 alkynyl group, optionally substituted with an alkyl group with 1 to 12 carbon atoms, with an alkoxy group with 1 to 12 carbon atoms, in particular with 1 to 8 carbon atoms, with a $CF_3$ group or in particular with a trimethylsilyl group, (iv) an aryl group having 1, 2 or 3 aromatic rings, in particular phenyl, or aralkyl with a C1-C12, in particular C1-C8 carbon chain, the aryl or aralkyl group being optionally substituted with a C1-C12, in particular C1-C8 alkyl group, or with a C1-C12, in particular C1-C8 alkoxy group, such as a methoxy, with a $CF_3$ group, or in particular with a trimethylsilyl group (v) a C3-C7 cycloalkyl, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl group, or (vi) a polymer represented by the formula $-(CH_2CH_2O)_n-R'$ or a polymer represented by the formula $-(CH_2CH_2CH_2O)_n-R'$, in which n=1 to 40, in particular n=1 to 20, and R' is a C1-C12, in particular C1-C8 alkyl group, then:

$L_2$ represents:

(i) an amine of formula

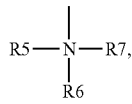

in which R5, R6 and R7 represent, independently of one another:

(a) a hydrogen, (b) a linear or branched C1-C18 alkyl, optionally substituted with an estradiol, (c) an aryl group having 1, 2 or 3 aromatic rings, in particular phenyl, or aralkyl with a C1-C12, in particular C1-C8 carbon chain, the aryl, aralkyl group being optionally substituted with a C1-C12, in particular C1-C8 alkoxy group, such as a methoxy, or an alkyl group with 1 to 12 carbon atoms, in particular with 1 to 8 carbon atoms, with a $CF_3$ group or with a trimethylsilyl group, (d) a C3-C7 cycloalkyl, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl, (e) a polymer represented by the formula $-(CH_2CH_2O)_n-R'$ or the formula $-(CH_2CH_2CH_2O)_n-R'$, in which n=1 to 40, in particular n=1 to 20, and R' is a C1-C12, in particular C1-C8 alkyl group, optionally substituted with an estradiol, (ii) a diamine of general formula $NH_2-(CH_2)_n-NH_2$, n=1 to 12 carbon atoms, (iii) a triamine of general formula $NH_2-(CH_2)_n-NH-(CH_2)_m-NH_2$, n=1 to 12 carbon atoms, m=1 to 12 carbon atoms, (iv) a linear or branched amino alcohol with 2 to 20 carbon atoms, in particular prolinol, (v) a linear or branched amino ester with 2 to 20 carbon atoms, in particular with 2 to 10 carbon atoms, (vi) a linear or branched amino amide with 2 to 20 carbon atoms, in particular prolinamide, (vii) an amino acid in particular selected from the 20 proteinogenic α-amino acids or their esters or amides, and in particular selected from alanine or its esters or amides, arginine or its esters or amides, asparagine or its esters or amides, aspartate or its esters or amides, cysteine or its esters or amides, glutamate or its esters or amides, glutamine or its esters or amides, glycine or its esters or amides, isoleucine or its esters or amides, leucine or its esters or amides, lysine or its esters or amides, methionine or its esters or amides, serine or its esters or amides, threonine or its esters or amides, valine or its esters or amides, (viii) a beta or gamma amino acid or its esters or amides, (ix) a peptide, optionally cyclic, comprising 2 to 30 amino acids, in particular from 2 to 10, (x) a morpholine, (xi) a piperazine optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl, (xii) a piperazine N-substituted with a dansyl or dabsyl group (xiii) a hydrazine monosubstituted with an aryl having 1, 2 or 3 aromatic rings, in particular a phenyl, or a linear or branched alkyl with 1 to 12 carbon atoms, (xiv) a glucamine optionally N-substituted with an alkyl group with 1 to 20 carbon atoms, in particular N-methylglucamine, N-ethylglucamine or N-dodecylglucamine, (xv) a glucosamine optionally N-substituted with an alkyl group with 1 to 20 carbon atoms (xvi) a pseudopeptide of general formula $H-(NH-CH(R)-CH_2-X-CO)_n-NHR''$, with R being a side chain of one of the 20 proteinogenic amino acids; X being independently, throughout the sequence, $CH_2$, O or NH; n=1-15; R''=H, or a short alkyl or aralkyl chain, (xvii) a pseudopeptide of general formula $R_a-CO-CH(R_b)-NH-CO-NH-CH(R_c)-CO-R_d$ in which $R_a$ and $R_d$ represent, independently of one another, H, a linear or branched C1-C6 alkyl group, a C3-C7 monocyclic cycloalkyl group, or a carboxylic acid protective group; $R_b$ represents the side chain of lysine, the amine of said side chain being optionally substituted with a $-CO-(CH_2)_5-NH_2$ group; $R_c$ represents a side chain of one of the 20 proteinogenic amino acids, optionally protected by an ad hoc protective group; and (xviii) a polymer represented by the general formula $NH_2-(CH_2(CH_2)_iNH)_{(n-1)}-H$, in which i=1, 2 or 3, n=1 to 1000, in particular n=1 to 500, more particularly from 1 to 100, said polymer forming moreover m-1 coordination bonds with m-1 groups of formula 1:

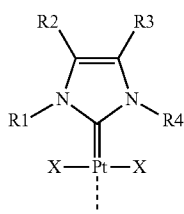

where $R_1$, $R_2$, $R_3$, $R_4$ and X are as defined above,
the number m being comprised between 1 and n, the ratio m/n representing the number of platinum atoms to the number of amines of —NH— or —$NH_2$ type, in particular being comprised between 1/50 and 1/2, more particularly between 1/20 and 1/2,
and X represents iodine, bromine or chlorine.

In a particularly advantageous embodiment, the process according to the invention makes it possible to obtain platinum-carbene complexes of the following formula II:

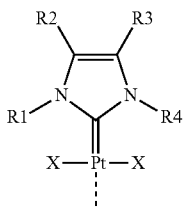

Formule II in which
(I) if:
R1 and R4 represent, independently of one another:
  (i) a linear or branched C1-C12, in particular C1-C8 alkyl group, optionally substituted with an alkoxy group with 1 to 12 carbon atoms, in particular with 1 to 8 carbon atoms, with a $CF_3$ group or in particular with a trimethylsilyl group,
  (ii) a linear or branched C2-C12, in particular C2-C8 alkenyl group, optionally substituted with an alkyl group with 1 to 12 carbon atoms, with an alkoxy group with 1 to 12 carbon atoms, in particular with 1 to 8 carbon atoms, with a $CF_3$ group, or in particular with a trimethylsilyl group,
  (iii) a linear or branched C2-C12, in particular C2-C8 alkynyl group, optionally substituted with an alkyl group with 1 to 12 carbon atoms, with an alkoxy group with 1 to 12 carbon atoms, in particular with 1 to 8 carbon atoms, with a $CF_3$ group, or in particular with a trimethylsilyl group,
  (iv) an aryl group having 1, 2 or 3 aromatic rings, in particular phenyl, or aralkyl with a C1-C12, in particular C1-C8 carbon chain, the aryl or aralkyl group being optionally substituted with a C1-C12, in particular C1-C8 alkyl group, or with a C1-C12, in particular C1-C8 alkoxy group, such as a methoxy, with a $CF_3$ group, or in particular with a trimethylsilyl group,
  (v) a C3-C7 cycloalkyl, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl group, or
  (vi) a polymer represented by the formula —($CH_2CH_2O$)$_n$—R' or a polymer represented by the formula —($CH_2CH_2CH_2O$)$_n$—R', in which n=1 to 40, in particular n=1 to 20, and R' is a C1-C12, in particular C1-C8 alkyl group, and R2 and R3 represent, independently of one another:
  a hydrogen,
  an aryl or aralkyl group, in particular phenyl, benzyl, or
  a linear or branched C2-C12, in particular C2-C8 alkynyl group, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl group, then $L_2$ represents:
  (i) a peptide, optionally cyclic, comprising 2 to 30, in particular 2 to 10 and in particular 2 to 3, amino acids, where the C-terminal acid and the N-terminal amine of said peptide and the side chains of said amino acids can be substituted with one or more substituent(s) selected independently from:
    a linear or branched C1-C6 alkyl,
    an aryl group having 1, 2 or 3 aromatic rings, in particular phenyl, or aralkyl with a C1-C12, in particular C1-C8 carbon chain,
    a C3-C7 cycloalkyl, optionally substituted with an alkyl group with 1 to 12 carbon atoms, in particular with 1 to 8 carbon atoms,
  (ii) a pseudopeptide of general formula H—(NH—CH(R)—$CH_2$—Y—CO)$_n$—NHR'', with R being a side chain of one of the 20 proteinogenic amino acids; Y being independently, throughout the sequence, $CH_2$, O or NH; n=1-15; R''=H, or a short alkyl or aralkyl chain,
  (iii) a pseudopeptide of general formula $R_a$—CO—CH($R_b$)—NH—CO—NH—CH($R_c$)—CO—$R_d$ in which $R_a$ and $R_d$ represent, independently of one another, H, a linear or branched C1-C6 alkyl group, a C3-C7 monocyclic cycloalkyl group, or a carboxylic acid protective group; $R_b$ represents the side chain of lysine, the amine of said side chain being optionally substituted with a —CO—($CH_2$)$_5$—$NH_2$ group; $R_c$ represents a side chain of one of the 20 proteinogenic amino acids, optionally protected by an ad hoc protective group,
  (iv) a polymer represented by the general formula $NH_2$—($CH_2(CH_2)_i NH$)$_{(n-1)}$—H, in which i=1, 2 or 3, n=1 to 1000, in particular n=1 to 500, more particularly from 1 to 100, said polymer forming moreover m-1 coordination bonds with m-1 groups of formula 1:

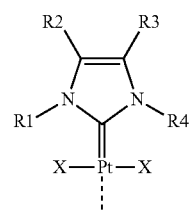

where $R_1$, $R_2$, $R_3$, $R_4$ and X are as defined above,
the number m being comprised between 1 and n, the ratio m/n representing the number of platinum atoms to the number of amines of type —NH— or —$NH_2$, in particular being comprised between 1/50 and 1/2, more particularly between 1/20 and 1/2,
and X represents iodine, bromine or chlorine;

(IIa) if:
R1 and R4 represent, independently of one another:
(i) a linear or branched C1-C12, in particular C1-C8 alkyl group, optionally substituted with an alkoxy group with 1 to 12 carbon atoms, in particular with 1 to 8 carbon atoms, with a $CF_3$ group or in particular with a trimethylsilyl group,
(ii) a linear or branched C2-C12, in particular C2-C8 alkenyl group, optionally substituted with an alkyl group with 1 to 12 carbon atoms, with an alkoxy group with 1 to 12 carbon atoms, in particular with 1 to 8 carbon atoms, with a $CF_3$ group or in particular with a trimethylsilyl group,
(iii) a linear or branched C2-C12, in particular C2-C8 alkynyl group, optionally substituted with an alkyl group with 1 to 12 carbon atoms, with an alkoxy group with 1 to 12 carbon atoms, in particular with 1 to 8 carbon atoms, with a $CF_3$ group or in particular with a trimethylsilyl group,
(iv) an aryl group having 1, 2 or 3 aromatic rings, in particular phenyl, or aralkyl with a C1-C12, in particular C1-C8 carbon chain, the aryl or aralkyl group being optionally substituted with a C1-C12, in particular C1-C8 alkyl group, or with a C1-C12, in particular C1-C8 alkoxy group, such as a methoxy, with a $CF_3$ group, or in particular with a trimethylsilyl group,
(v) a C3-C7 cycloalkyl, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl group, or
(vi) a polymer represented by the formula —$(CH_2CH_2O)_n$—R' or a polymer represented by the formula —$(CH_2CH_2CH_2O)_n$—R', in which n=1 to 40, in particular n=1 to 20, and R' is a C1-C12, or in particular C1-C8, alkyl group,
with the condition that R1 or R4 represents:
a linear or branched C1-C6 alkyl group, substituted with a trimethylsilyl group,
an aryl group having 2 or 3 aromatic rings, in particular naphthalenyl or anthracenyl, the aryl group being optionally substituted with a C1-C12, in particular C1-C8 alkyl group, or with a C1-C12, in particular C1-C8 alkoxy group, such as a methoxy, with a $CF_3$ group, or in particular with a trimethylsilyl group,
a linear or branched C2-C12, in particular C2-C8 alkynyl group, optionally substituted with an alkyl group with 1 to 12 carbon atoms, with an alkoxy group with 1 to 12 carbon atoms, in particular with 1 to 8 carbon atoms, with a $CF_3$ group or in particular with a trimethylsilyl group,
a polymer represented by the formula —$(CH_2CH_2O)_n$—R' or a polymer represented by the formula —$(CH_2CH_2CH_2O)_n$—R', in which n=1 to 40, in particular n=1 to 20, and R' is a C1-C12, in particular C1-C8 alkyl group,
and R2 and R3 represent, independently of one another:
a hydrogen,
an aryl or aralkyl group, in particular phenyl, benzyl, or
a linear or branched C2-C12, in particular C2-C8 alkynyl group, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl group, II (b) or, if:
R2 and R3 represent, independently of one another:
a hydrogen,
an aryl or aralkyl group, in particular phenyl, benzyl, or
a linear or branched C2-C12, in particular C2-C8 alkynyl group, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl group, provided that R2 or R3 represents:
a linear or branched C2-C12, in particular C2-C8 alkynyl, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl group,
and R1 and R4 represent, independently of one another:
(i) a linear or branched C1-C12, in particular C1-C8 alkyl group, optionally substituted with an alkoxy group with 1 to 12 carbon atoms, in particular with 1 to 8 carbon atoms, with a $CF_3$ group or in particular with a trimethylsilyl group,
(ii) a linear or branched C2-C12, in particular C2-C8 alkenyl group, optionally substituted with an alkyl group with 1 to 12 carbon atoms, with an alkoxy group with 1 to 12 carbon atoms, in particular with 1 to 8 carbon atoms, with a $CF_3$ group or in particular with a trimethylsilyl group,
(iii) a linear or branched C2-C12, in particular C2-C8 alkynyl group, optionally substituted with an alkyl group with 1 to 12 carbon atoms, with an alkoxy group with 1 to 12 carbon atoms, in particular with 1 to 8 carbon atoms, with a $CF_3$ group or in particular with a trimethylsilyl group,
(iv) an aryl group having 1, 2 or 3 aromatic rings, in particular phenyl, or aralkyl with a C1-C12, in particular C1-C8 carbon chain, the aryl or aralkyl group being optionally substituted with a C1-C12, in particular C1-C8 alkyl group, or with a C1-C12, in particular C1-C8 alkoxy group, such as a methoxy, with a $CF_3$ group, or in particular with a trimethylsilyl group
(v) a C3-C7 cycloalkyl, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl group, or
(vi) a polymer represented by the formula —$(CH_2CH_2O)_n$—R' or a polymer represented by the formula —$(CH_2CH_2CH_2O)_n$—R', in which n=1 to 40, in particular n=1 to 20, and R' is a C1-C12, in particular C1-C8 alkyl group,
then:
$L_2$ represents:
(i) an amine of formula

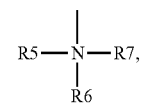

in which R5, R6 and R7 represent, independently of one another:
- (a) a hydrogen,
- (b) a linear or branched, non-cyclized C1-C18 alkyl, optionally substituted with an estradiol,
- (c) an aryl group having 1, 2 or 3 aromatic rings, in particular phenyl, or aralkyl with a C1-C12, in particular C1-C8 carbon chain, the aryl, aralkyl group being optionally substituted with a C1-C12, in particular C1-C8 alkoxy group, such as a methoxy, or an alkyl group with 1 to 12 carbon atoms, in particular with 1 to 8 carbon atoms, with a $CF_3$ group or with a trimethylsilyl group,
- (d) a C3-C7 cycloalkyl, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl,
- (e) a polymer represented by the formula $-(CH_2CH_2O)_n-R'$ or the formula $-(CH_2CH_2CH_2O)_n-R'$, in which n=1 to 40, in particular n=1 to 20, and R' is a C1-C12, in particular C1-C8 alkyl group, optionally substituted with an estradiol,
- (ii) a diamine of general formula $NH_2-(CH_2)_n-NH_2$, n=1 to 12 carbon atoms,
- (iii) a triamine of general formula $NH_2-(CH_2)_n-NH-(CH_2)_{n'}-NH_2$, n=1 to 12 carbon atoms, n'=1 to 12 carbon atoms,
- (iv) a linear or branched amino alcohol with 2 to 20 carbon atoms, in particular prolinol,
- (v) a linear or branched amino ester with 2 to 20 carbon atoms, in particular with 2 to 10 carbon atoms,
- (vi) a linear or branched amino amide with 2 to 20 carbon atoms, in particular prolinamide,
- (vii) an amino acid in particular selected from the 20 proteinogenic α-amino acids or their esters or amides, and in particular alanine or its esters or amides, arginine or its esters or amides, asparagine or its esters or amides, aspartate or its esters or amides, cysteine or its esters or amides, glutamate or its esters or amides, glutamine or its esters or amides, glycine or its esters or amides, isoleucine or its esters or amides, leucine or its esters or amides, lysine or its esters or amides, methionine or its esters or amides, serine or its esters or amides, threonine or its esters or amides, valine or its esters or amides,
- (viii) a beta or gamma amino acid or its esters or amides,
- (ix) a peptide, optionally cyclic, comprising 2 to 30, in particular 2 to 10 and in particular 2 to 3, amino acids, where the C-terminal acid and the N-terminal amine of said peptide and the side chains of said amino acids can be substituted with one or more substituent(s) selected independently from:
  - a linear or branched C1-C6 alkyl,
  - an aryl group having 1, 2 or 3 aromatic rings, in particular phenyl, or aralkyl with a C1-C12, in particular C1-C8 carbon chain,
  - a C3-C7 cycloalkyl, optionally substituted with an alkyl group with 1 to 12 carbon atoms, in particular with 1 to 8 carbon atoms,
- (x) a morpholine,
- (xi) a piperazine optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl,
- (xii) a piperazine N-substituted with a dansyl or dabsyl group
- (xiii) a hydrazine monosubstituted with an aryl having 1, 2 or 3 aromatic rings, in particular a phenyl, or a linear or branched alkyl with 1 to 12 carbon atoms,
- (xiv) a glucamine optionally N-substituted with an alkyl group with 1 to 20 carbon atoms, in particular N-methylglucamine, N-ethylglucamine or N-dodecylglucamine,
- (xv) a glucosamine optionally N-substituted with an alkyl group with 1 to 20 carbon atoms
- (xvi) a pyridine or a pyridine substituted with iodine, bromine or chlorine, in particular 3-bromopyridine, or 3-chloropyridine, or disubstituted with iodine, bromine or chlorine, in particular 3,5-dibromopyridine
- (xvii) a pseudopeptide of general formula H—(NH—CH(R)—$CH_2$—Y—CO) n-NHR", with R being a side chain of one of the 20 proteinogenic amino acids; Y being independently, throughout the sequence, $CH_2$, O or NH; n=1-15; R"=H, or a short alkyl or aralkyl chain,
- (xviii) a pseudopeptide of general formula $R_a$—CO—CH($R_b$)—NH—CO—NH—CH($R_c$)—CO—$R_d$ in which $R_a$ and $R_d$ represent, independently of one another, H, a linear or branched C1-C6 alkyl group, a C3-C7 monocyclic cycloalkyl group, or a carboxylic acid protective group; $R_b$ represents the side chain of lysine, the amine of said side chain being optionally substituted with a —CO—$(CH_2)_5$—$NH_2$ group; $R_c$ represents a side chain of one of the 20 proteinogenic amino acids, optionally protected by an ad hoc protective group
- (xix) a polymer represented by the general formula $NH_2-(CH_2(CH_2)_iNH)_{(n-1)}$—H, in which i=1, 2 or 3, n=1 to 1000, in particular n=1 to 500, more particularly from 1 to 100, said polymer forming moreover m-1 coordination bonds with m-1 groups of formula 1:

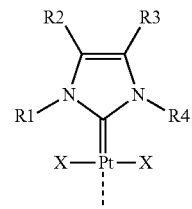

1 where $R_1$, $R_2$, $R_3$, $R_4$ and X are as defined above, the number m being comprised between 1 and n, the ratio m/n representing the number of platinum atoms to the number of amines of —NH— or —$NH_2$ type, in particular being comprised between 1/50 and 1/2, more particularly between 1/20 and 1/2, and X represents iodine, bromine or chlorine.

In a particularly advantageous embodiment, the process according to the invention makes it possible to obtain platinum-carbene complexes of the following formula II:

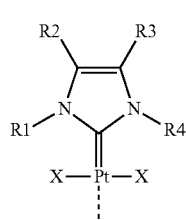

Formula II in which
R1 and R4 represent, independently of one another:
(i) a linear or branched C1-C12, in particular C1-C8 alkyl group, optionally substituted with an alkoxy group with 1 to 12 carbon atoms, in particular with 1 to 8 carbon atoms, with a $CF_3$ group or in particular with a trimethylsilyl group,
(ii) a linear or branched C2-C12, in particular C2-C8 alkenyl group, optionally substituted with an alkyl group with 1 to 12 carbon atoms, with an alkoxy group with 1 to 12 carbon atoms, in particular with 1 to 8 carbon atoms, with a $CF_3$ group, or in particular with a trimethylsilyl group,
(iii) a linear or branched C2-C12, in particular C2-C8 alkynyl group, optionally substituted with an alkyl group with 1 to 12 carbon atoms, with an alkoxy group with 1 to 12 carbon atoms, in particular with 1 to 8 carbon atoms, with a $CF_3$ group, or in particular with a trimethylsilyl group,
(iv) an aryl group having 1, 2 or 3 aromatic rings, in particular phenyl, or aralkyl with a C1-C12, in particular C1-C8 carbon chain, the aryl or aralkyl group being optionally substituted with a C1-C12, in particular C1-C8 alkyl group, or with a C1-C12, in particular C1-C8 alkoxy group, such as a methoxy, with a $CF_3$ group, or in particular with a trimethylsilyl group,
(v) a C3-C7 cycloalkyl, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl group, or
(vi) a polymer represented by the formula $-(CH_2CH_2O)_n-R'$ or a polymer represented by the formula $-(CH_2CH_2CH_2O)_n-R'$, in which n=1 to 40, in particular n=1 to 20, and R' is a C1-C12, in particular C1-C8 alkyl group,
R2 and R3 represent, independently of one another:
a hydrogen,
an aryl or aralkyl group, in particular phenyl, benzyl, or
a linear or branched C2-C12, in particular C2-C8 alkynyl group, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl group,
$L_2$ represents a polymer represented by the general formula $NH_2-(CH_2(CH_2)_iNH)_{(n-1)}-H$, in which i=1, 2 or 3, n=1 to 1000, in particular n=1 to 500, more particularly from 1 to 100, said polymer forming moreover m-1 coordination bonds with m-1 groups of formula 1:

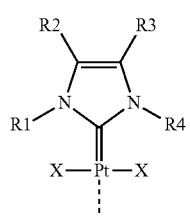

where $R_1$, $R_2$, $R_3$, $R_4$ and X are as defined above, the number m being comprised between 1 and n, the ratio m/n representing the number of platinum atoms to the number of amines of $-NH-$ or $-NH_2$ type, in particular being comprised between 1/50 and 1/2, more particularly between 1/20 and 1/2,
and X represents iodine, bromine or chlorine.

In a particularly advantageous embodiment, the process according to the invention makes it possible to obtain platinum-carbene complexes of the following formula IIa:

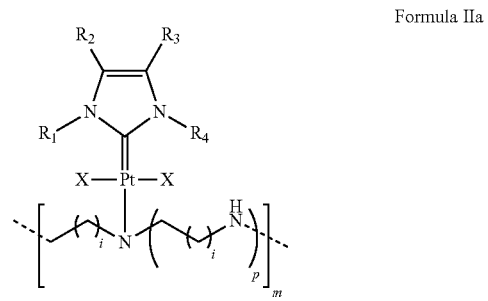

Formula IIa in which
R1 and R4 represent, independently of one another:
(i) a linear or branched C1-C12, in particular C1-C8 alkyl group, optionally substituted with an alkoxy group with 1 to 12 carbon atoms, in particular with 1 to 8 carbon atoms, with a $CF_3$ group or in particular with a trimethylsilyl group,
(ii) a linear or branched C2-C12, in particular C2-C8 alkenyl group, optionally substituted with an alkyl group with 1 to 12 carbon atoms, with an alkoxy group with 1 to 12 carbon atoms, in particular with 1 to 8 carbon atoms, with a $CF_3$ group, or in particular with a trimethylsilyl group,
(iii) a linear or branched C2-C12, in particular C2-C8 alkynyl group, optionally substituted with an alkyl group with 1 to 12 carbon atoms, with an alkoxy group with 1 to 12 carbon atoms, in particular with 1 to 8 carbon atoms, with a $CF_3$ group, or in particular with a trimethylsilyl group,
(iv) an aryl group having 1, 2 or 3 aromatic rings, in particular phenyl, or aralkyl with a C1-C12, in particular C1-C8 carbon chain, the aryl or aralkyl group being optionally substituted with a C1-C12, in particular C1-C8 alkyl group, or with a C1-C12, in particular C1-C8 alkoxy group, such as a methoxy, with a $CF_3$ group, or in particular with a trimethylsilyl group,
(v) a C3-C7 cycloalkyl, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl group, or
(vi) a polymer represented by the formula $-(CH_2CH_2O)_n-R'$ or a polymer represented by the formula $-(CH_2CH_2CH_2O)_n-R'$, in which n=1 to 40, in particular n=1 to 20, and R' is a C1-C12, in particular C1-C8 alkyl group,
and R2 and R3 represent, independently of one another:
a hydrogen,
an aryl or aralkyl group, in particular phenyl, benzyl, or
a linear or branched C2-C12, in particular C2-C8 alkynyl group, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a CF$_3$ group, or in particular with a trimethylsilyl group, X represents iodine, bromine or chlorine, m=1 to 1000, in particular m=1 to 100, more particularly from 1 to 50, p=0 to 50, in particular p=1 to 20, more particularly from 1 to 10, p representing the ratio of the number of platinum atoms to the number of amines of —NH— or —NH$_2$ type, i=1, 2 or 3, All of the products defined above are novel.

In a particularly advantageous embodiment, the process according to the invention makes it possible to obtain novel carbene complexes of the following formula II:

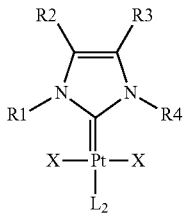

Formula II in which:

(I) if:

R1 and R4 represent, independently of one another: 2,5,8,11-tetraoxamidecane, a heptyl, a methyl, a benzyl;

R2 and R3 represent, independently of one another:
a hydrogen,
an alkyne substituted with a trimethylsilyl, X represents iodine, bromine or chlorine; and then L$_2$ represents:

valine or its esters, phenylalanine or its esters, Leu-Gly or Leu-Gly-OMe, Val-Phe-Gly or Val-Phe-Gly-OMe, Ile-Lys-Gly or Ile-Lys-Gly-OMe, (methoxy)polyethylene glycol amine, methyl 6-aminohexanoate, prolinol, prolinamide, ethanolamine, (6S,11S,16S,21S,26S)-6,21-diisobutyl-16-isopropyl-11-methyl-3,8,13,18,23-pentaoxo-2,4,7,9,12,14,17,19,22,24-decaazaheptacosan-26-aminium, N,N-dimethyl-5-(piperazin-1-ylsulphonyl)naphthalen-1-amine, phenylhydrazine, diethylenetriamine, ethylenediamine, linear poly(ethylenamine), (13S,16R,17R)-16-(7-aminoheptyl)-16-(hydroxymethyl)-13-methyl-7,8,9,11,12,13,14,15,16,17-decahydro-6H-cyclopenta[α]phenanthrene-3,17-diol, or 16(beta)hydroxymethyl-16-(amino[polyethyleneglycol])-1,3,5(10)-estratriene-3,17-diol, N—[N—[(S)-1,3-dicarboxypropyl]carbamoyl]-(S)-lysine, MeO-L-Lys-CO-L-Glu(OMe)-OMe, MeO-L-Lys(CO—(CH$_2$)$_5$—NH$_2$)—CO-L-Glu(OMe)-OMe, CCl$_3$—CH$_2$—O-L-Lys-CO-L-Glu(O—CH$_2$—CCl$_3$)—OCH$_2$CCl$_3$ or cyclic H-Arg(HCl)-Gly-Asp(CH$_2$CCl$_3$)-D-Phe-Lys(N$_3$)—OH, (IIa) if:

(i) R1 and R4 represent, independently of one another: 2,5,8,11-tetraoxamidecane, a heptyl, a methyl, a benzyl, with the condition that R1 or R4 represents 2,5,8,11-tetraoxamidecane or a heptyl, and (ii) R2 and R3 represent, independently of one another:
a hydrogen,
an alkyne substituted with a trimethylsilyl, (IIb) or if:

(i) R2 and R3 represent, independently of one another, a hydrogen or an alkyne substituted with a trimethylsilyl, with the condition that R2 or R3 represents an alkyne substituted with a trimethylsilyl, (ii) R1 and R4 represent, independently of one another: 2,5,8,11-tetraoxamidecane, a heptyl, a methyl, a benzyl;

then:

L$_2$ represents:

NH$_3$$^+$, cyclohexylamine, morpholine, valine or its esters, phenylalanine or its esters, Leu-Gly or Leu-Gly-OMe, Val-Phe-Gly or Val-Phe-Gly-OMe, Ile-Lys-Gly or Ile-Lys-Gly-OMe, (methoxy)polyethylene glycol amine, methyl 6-aminohexanoate, prolinol, prolinamide, ethanolamine, (6S,11S,16S,21S,26S)-6,21-diisobutyl-16-isopropyl-11-methyl-3,8,13,18,23-pentaoxo-2,4,7,9,12,14,17,19,22,24-decaazaheptacosan-26-aminium, N,N-dimethyl-5-(piperazin-1-ylsulphonyl)naphthalen-1-amine, phenylhydrazine, diethylenetriamine, ethylenediamine, linear poly(ethylenamine), (13S,16R,17R)-16-(7-aminoheptyl)-16-(hydroxymethyl)-13-methyl-7,8,9,11,12,13,14,15,16,17-decahydro-6H-cyclopenta[α]phenanthrene-3,17-diol, or 16(beta)hydroxymethyl-16-(amino[polyethyleneglycol])-1,3,5(10)-estratriene-3,17-diol, N—[N—[(S)-1,3-dicarboxypropyl]carbamoyl]-(S)-lysine, MeO-L-Lys-CO-L-Glu(OMe)-OMe, MeO-L-Lys(CO—(CH$_2$)$_5$—NH$_2$)—CO-L-Glu(OMe)-OMe, CCl$_3$—CH$_2$—O-L-Lys-CO-L-Glu(O—CH$_2$—CCl$_3$)—OCH$_2$CCl$_3$ or cyclic H-Arg(HCl)-Gly-Asp(CH$_2$CCl$_3$)-D-Phe-Lys(N$_3$)—OH, X represents iodine, bromine or chlorine.

In another particular embodiment, the process according to the invention makes it possible to obtain platinum-carbene complexes of the following formula II:

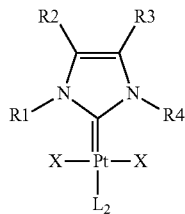

Formula II in which L$_2$ represents NH$_3$$^+$, —NH$_2$-benzyl optionally substituted with a CF$_3$ group, a cyclohexyl, or a morpholine R1 and R4 represent, independently of one another:
a linear or branched C1-C6 alkyl group, in particular a methyl,
a phenyl, or a benzyl, optionally substituted with an alkoxy group with 1 to 12 carbon atoms, or with a CF$_3$ group,
a linear or branched C2-C8 alkenyl group,
a C3-C7 cycloalkyl, R2 and R3 represent, independently of one another:
a hydrogen,
a phenyl group, and X represents iodine, bromine or chlorine.

In another particular embodiment, the process according to the invention makes it possible to obtain water-soluble platinum-carbene complexes.

These complexes are represented by the following formula II:

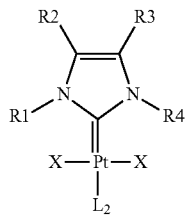

Formula II in which:
R1 and R4 represent, independently of one another:
(i) a linear or branched C1-C12, in particular C1-C8 alkyl group, optionally substituted with an alkoxy group with 1 to 12 carbon atoms, in particular with 1 to 8 carbon atoms, with a $CF_3$ group or in particular with a trimethylsilyl group,
(ii) a linear or branched C2-C12, in particular C2-C8 alkenyl group, optionally substituted with an alkyl group with 1 to 12 carbon atoms, with an alkoxy group with 1 to 12 carbon atoms, in particular with 1 to 8 carbon atoms, with a $CF_3$ group, or in particular with a trimethylsilyl group,
(iii) a linear or branched C2-C12, in particular C2-C8 alkynyl group, optionally substituted with an alkyl group with 1 to 12 carbon atoms, with an alkoxy group with 1 to 12 carbon atoms, in particular with 1 to 8 carbon atoms, with a $CF_3$ group, or in particular with a trimethylsilyl group,
(iv) an aryl group having 1, 2 or 3 aromatic rings, in particular phenyl, or aralkyl with a C1-C12, in particular C1-C8 carbon chain, the aryl or aralkyl group being optionally substituted with a C1-C12, in particular C1-C8 alkyl group, or with a C1-C12, in particular C1-C8 alkoxy group, such as a methoxy, with a $CF_3$ group, or in particular with a trimethylsilyl group,
(v) a C3-C7 cycloalkyl, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl group, or
(vi) a polymer represented by the formula —$(CH_2CH_2O)_n$—R' or a polymer represented by the formula —$(CH_2CH_2CH_2O)_n$—R', in which n=1 to 40, in particular n=1 to 20, and R' is a C1-C12, in particular C1-C8 alkyl group,
and R2 and R3 represent, independently of one another:
a hydrogen,
an aryl or aralkyl group, in particular phenyl, benzyl, or
a linear or branched C2-C12, in particular C2-C8 alkynyl group, optionally substituted with an alkyl group with 1 to 12 carbon atoms, in particular with 1 to 8 carbon atoms, with an alkoxy group with 1 to 12 carbon atoms, in particular with 1 to 8 carbon atoms, with a $CF_3$ group, or in particular with a trimethylsilyl group,
and $L_2$ represents:
(i) an amine of formula

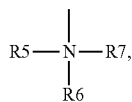

in which:
at least one of the R5, R6 and R7 radicals represents a polymer represented by the formula —$(CH_2CH_2O)_n$—R' or the formula —$(CH_2CH_2CH_2O)_n$—R', in which n=6 to 40, in particular n=6 to 20, and R' is a C1-C12, in particular C1-C8 alkyl group,
R5, R6 and R7 represent, independently of one another:
(a) a hydrogen,
(b) a linear or branched, non-cyclized C1-C18 alkyl, optionally substituted with an estradiol,
(c) an aryl having 1 or 2 or 3 aromatic rings, in particular phenyl, optionally substituted with a C1-C12, in particular C1-C8 alkoxy group, such as a methoxy, or an alkyl group with 1 to 12 carbon atoms, in particular with 1 to 8 carbon atoms, with a $CF_3$ group, or in particular with a trimethylsilyl,
(d) a polymer represented by the formula —$(CH_2CH_2O)_n$—R' or the formula —$(CH_2CH_2CH_2O)_n$—R', in which n=6 to 40, in particular n=6 to 20, and R' is a C1-C12, in particular C1-C8 alkyl group, optionally substituted with an estradiol,
(ii) a diamine of general formula $NH_2$—$(CH_2)_n$—$NH_2$, n=1 to 12 carbon atoms,
(iii) a triamine of general formula $NH_2$—$(CH_2)_n$—$NH$—$(CH_2)_m$—$NH_2$, n=1 to 12 carbon atoms, m=1 to 12 carbon atoms,
(iv) a polymer represented by the general formula $NH_2$—$(CH_2(CH_2)_iNH)_{(n-1)}$—H, in which i=1, 2 or 3, n=1 to 1000, in particular n=1 to 500, more particularly from 1 to 100, said polymer forming moreover m-1 coordination bonds with m-1 groups of formula 1:

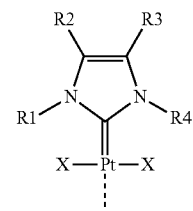

where $R_1$, $R_2$, $R_3$, $R_4$ and X are as defined above,
the number m being comprised between 1 and n, the ratio m/n representing the number of platinum atoms to the number of amines of —NH— or —$NH_2$ type, in particular being comprised between 1/50 and 1/2, more particularly between 1/20 and 1/2.

The following examples describe the preparation of certain compounds of formula II according to diagram I. These examples are not limitative and are only intended to illustrate the present invention.

Equipment and Methods:

The $^1$H NMR spectrum is measured on a Brucker Avance 300 spectrometer. The frequencies are 300 MHz for proton spectroscopy ($^1$H NMR).

The $^{13}$C NMR spectrum is measured on a Brucker Avance 300 spectrometer. The frequencies are 75 MHz for carbon spectroscopy ($^{13}$C NMR). The chemical shifts (δ) are stated in parts per million (ppm), using the residual signals of the deuterated solvent as reference.

X-ray diffraction (ORTEP diagrams) was carried out on a Nonius Kappa-CCD or Bruker APEX II DUO Kappa-CCD diffractometer.

EXAMPLE 1 trans-diiodo(N-cyclohexylamine)[1-methyl-3-(2,5,8,11-tetraoxamidecan-13-yl)-imidazol-2-ylidene]platinum(II)

The compound trans-diiodo(N-pyridine)[1-methyl-3-(2,5,8,11-tetraoxamidecan-13-yl-imidazol-2-ylidene]platinum (II) (15 mg; 0.019 mmol) is suspended in ethanol (1 mL). Cyclohexylamine (25 μL; 0.218 mmol) is added. The reaction medium is held at 55° C. for 20 h. The ethanol is evaporated off and the crude product is washed with pentane and then purified by flash chromatography, eluting with a mixture of dichloromethane and methanol (20/1 by volume). This gives 14 mg (93%) of trans-diiodo(N-cyclohexylamine)[1-methyl-3-(2,5,8,11-tetraoxamidecan-13-yl)-imidazol-2-ylidene]platinum(II), represented by the following chemical structure:

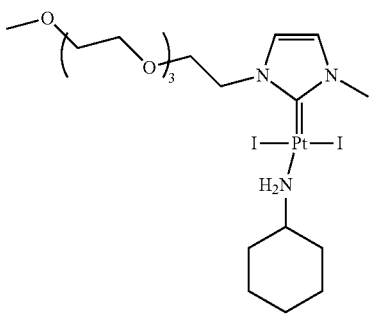

in the form of a yellow oil, which has the following characteristics:

$^1$H NMR spectrum (CDCl$_3$): δ 1.10-1.45 (m, 5H); 1.50-2.35 (m, 5H); 2.70-3.05 (m, 2H); 3.24 (m, 1H); 3.38 (s, 3H); 3.55 (m, 2H); 3.61-3.67 (m; 10H); 3.85 (s, 3H); 3.96 (t, 2H); 4.68 (t, 2H); 6.77 (d, 1H); 7.07 (d, 1H);

$^{13}$C NMR spectrum (CDCl$_3$): δ 25.0; 25.5; 36.1; 38.2; 50.6; 55.0; 59.3; 69.7; 70.4; 70.5; 70.6; 72.2; 121.6; 122.6; 138.9;

Mass spectrum (positive ESI mode): calculated for C$_{19}$H$_{37}$N$_3$I$_2$O$_4$PtNa: 843.04. found: 843.05.

EXAMPLE 2 trans-diiodo(N-cyclohexylamine)[1,3-di(2,5,8,11-tetraoxamidecan-13-yl)-imidazol-2-ylidene]platinum (II)

The compound trans-diiodo(N-pyridine) [1,3-di(2,5,8,11-tetraoxamidecan-13-yl)-imidazol-2-ylidene]platinum(II) (28 mg; 0.029 mmol) is suspended in ethanol (2 mL). Cyclohexylamine (33 μL; 0.282 mmol) is added. The reaction medium is held at 55° C. for 20 h. The ethanol is evaporated off and the crude product is washed with pentane and then purified by flash chromatography, eluting with a mixture of dichloromethane and methanol (20/1 by volume). This gives 18 mg (62%) of trans-diiodo(N-cyclohexylamine)[1,3-di(2,5,8,11-tetraoxamidecan-13-yl)-imidazol-2-ylidene]platinum(II), represented by the following chemical structure:

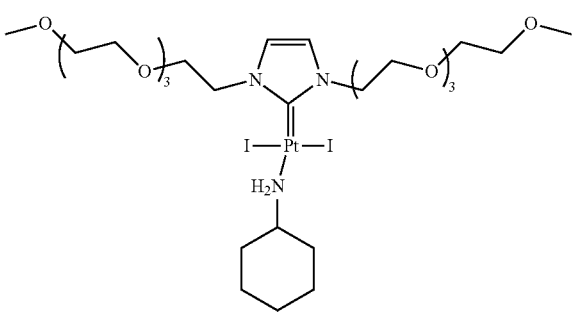

in the form of a yellow oil, which has the following characteristics:

$^1$H NMR spectrum (CDCl$_3$): δ 1.10-1.45 (m, 5H); 1.50-2.35 (m, 5H); 2.70-3.05 (m, 2H); 3.24 (m, 1H); 3.38 (s, 6H); 3.55 (m, 4H); 3.61-3.67 (m; 20H); 3.96 (t, 4H); 4.55 (t, 4H); 7.02 (s, 2H);

$^{13}$C NMR spectrum (CDCl$_3$): δ 24.8; 25.3; 35.9; 50.5; 54.7; 59.0; 69.4; 70.4; 70.5; 70.6; 72.0; 121.9; 138.0;

Mass spectrum (positive ESI mode): calculated for C$_{27}$H$_{53}$N$_3$I$_2$O$_8$PtNa: 1019.15. found: 1019.14.

EXAMPLE 3 trans-diiodo(N-cyclohexylamine)[1-methyl-3-heptyl-imidazol-2-ylidene]platinum(II)

The compound trans-diiodo(N-pyridine)[1-methyl-3-heptyl-imidazol-2-ylidene]platinum(II) (34 mg; 0.048 mmol) is suspended in ethanol (2 mL). Cyclohexylamine (50 μL; 0.437 mmol) is added. The reaction medium is held at 79° C. for 20 h. The ethanol is evaporated off and the crude product is purified by flash chromatography, eluting with dichloromethane. This gives 36 mg (100%) of trans-diiodo(N-cyclohexylamine)[1-methyl-3-heptyl-imidazol-2-ylidene]platinum(II), represented by the following chemical structure,

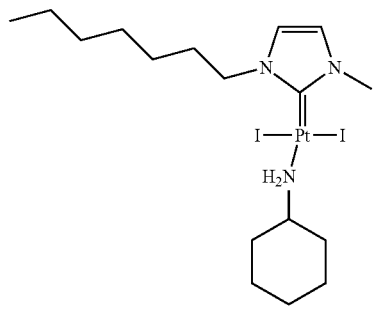

in the form of a yellow oil, which has the following characteristics:

$^1$H NMR spectrum (CDCl$_3$): δ 0.89 (t, 3H); 1.10-1.54 (m, 13H); 1.50-2.35 (t, 7H); 2.82 (m, 2H); 3.52 (m, 1H); 3.86 (s, 3H); 4.31 (t, 2H); 6.80 (s, 2H);

$^{13}$C NMR spectrum (CDCl$_3$): δ 14.1; 22.6; 24.8; 25.3; 26.7; 28.9; 29.7; 31.7; 35.9; 38.1; 50.8; 54.8; 120.3; 121.7; 138.7;

Mass spectrum (positive ESI mode): calculated for (C$_{17}$H$_{33}$N$_3$I$_2$Pt)$_2$Na: 1479.07. found: 1479.07.

EXAMPLE 4 trans-diiodo(N-cyclohexylamine)[1-methyl-3-benzyl-5-((trimethylsilyl)ethynyl)-imidazol-2-ylidene]platinum(II)

The compound trans-diiodo(N-pyridine)[1-methyl-3-benzyl-5-(trimethylsilyl)ethynyl-imidazol-2-ylidene]platinum(II) (34 mg; 0.048 mmol) is solubilized in cyclohexylamine (1 mL). The reaction medium is stirred at room temperature for 10 min. The cyclohexylamine is evaporated off and the crude product is washed with pentane and with ether. This gives 15 mg (48%) of trans-diiodo(N-cyclohexylamine)[1-methyl-3-benzyl-5-((trimethylsilyl)ethynyl)-imidazol-2-ylidene]platinum(II), represented by the following chemical structure,

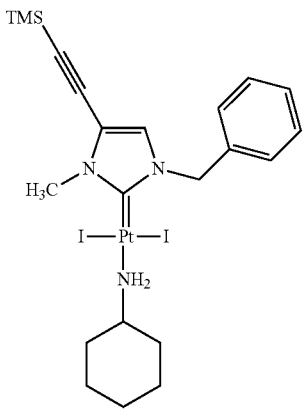

in the form of a yellow powder, which has the following characteristics:

¹H NMR spectrum (CDCl₃): δ 0.21 (s, 9H); 1.07-1.40 (m, 5H); 1.71-1.83 (m, 5H); 2.95 (d, 2H); 3.26 (m, 1H); 3.88 (s, 3H); 5.55 (s, 2H); 6.73 (s, 1H); 7.32-7.46 (m, 5H)

¹³C NMR spectrum (CDCl₃): δ-0.4; 24.8; 25.3; 35.9; 36.0; 54.7; 54.9; 90.3; 104.7; 123.8; 128.5; 128.9; 129.2; 134.9; 141.9

Mass spectrum (positive ESI mode): calculated for $C_{22}H_{33}N_3PtSi$: 689.11. found: 689.13.

ORTEP diagram shown below: obtained by X-ray diffraction. Crystals obtained from a solution in dichloromethane, by slow diffusion of pentane.

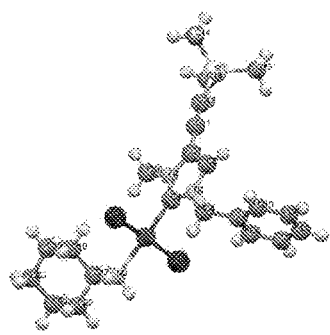

EXAMPLE 5 trans-diiodo(N-morpholine)[1-methyl-3-benzyl-5-((trimethylsilyl)ethynyl)-imidazol-2-ylidene]platinum(II)

The compound trans-diiodo(N-pyridine)[1-methyl-3-benzyl-5-(trimethylsilyl)ethynyl-imidazol-2-ylidene]platinum (II) (48 mg; 0.061 mmol) is solubilized in morpholine (2 mL). The reaction medium is stirred at room temperature for 10 min. The cyclohexylamine is evaporated off and the crude product is washed with pentane and with ether. This gives 47 mg (86%) of trans-diiodo(N-morpholine)[1-methyl-3-benzyl-5-((trimethylsilyl)ethynyl)-imidazol-2-ylidene]platinum (II), represented by the following chemical structure,

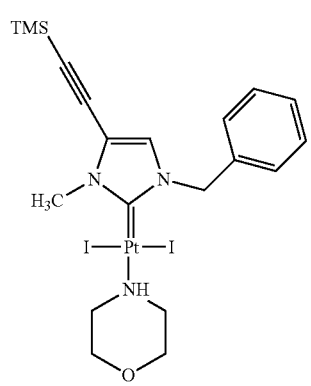

in the form of a yellow powder, which has the following characteristics:

¹H NMR spectrum (CDCl₃): δ 0.21 (s, 9H); 2.86 (m, 2H); 3.41 (m, 1H); 3.50-3.75 (m, 6H); 3.60-3.90 (m, 5H); 5.52 (s, 2H); 6.73 (s, 1H); 7.32-7.46 (m, 5H)

¹³C NMR spectrum (CDCl₃): δ 0.0; 36.2; 54.9; 68.8; 90.2; 104.8; 118.3; 123.9; 128.6; 128.9; 129.2; 129.3; 134.7; 138.2

Mass spectrum (positive ESI mode): calculated for $C_{20}H_{29}N_3PtSiO$: 677.08. found: 677.08.

ORTEP diagram shown below: obtained by X-ray diffraction. Crystals obtained from a solution in dichloromethane, by slow diffusion of pentane.

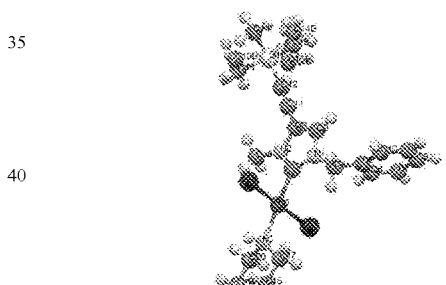

EXAMPLE 6 trans-diiodo(N-ammonia)[1-methyl-3-benzyl-imidazol-2-ylidene]platinum(II)

The compound trans-diiodo(N-pyridine) [1-methyl-3-benzyl-imidazol-2-ylidene]platinum(II) (28 mg; 0.040 mmol), ammonium chloride (9 mg; 0.168 mmol) and triethylamine (20 μL; 0.148 mmol) are suspended in ethanol (1 mL). The reaction medium is held at 55° C. for 24 h. The solvent is evaporated off, and the crude product is washed with pentane and purified by flash chromatography, eluting with a mixture of dichloromethane and cyclohexane (3/1 by volume) and then with dichloromethane. This gives 12 mg (48%) of trans-diiodo(N-ammonia)[1-methyl-3-benzyl-imidazol-2-ylidene]platinum(II), represented by the following chemical structure,

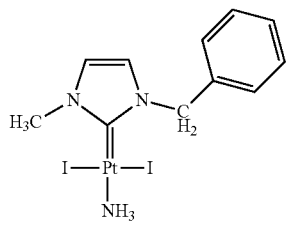

in the form of a yellow powder, which has the following characteristics:

$^1$H NMR spectrum (CDCl$_3$): δ 2.64 (m, 3H); 3.90 (s, 3H); 5.61 (s, 2H); 6.59 (d, 1H); 6.80 (d, 1H); 7.34-7.46 (m, 5H)

ORTEP diagram shown below: obtained by X-ray diffraction. Crystals obtained from a solution in dichloromethane, by slow diffusion of pentane.

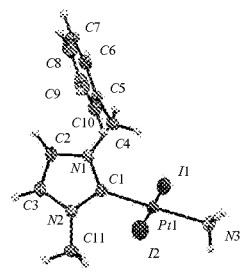

EXAMPLE 7 trans-diiodo(N-(L)-valine methyl ester)[1-methyl-3-benzyl-imidazol-2-ylidene]platinum(II)

The compound trans-diiodo(N-pyridine)[1-methyl-3-benzyl-imidazol-2-ylidene]platinum(II) (54 mg; 0.077 mmol), (L)-valine methyl ester hydrochloride (16 mg; 0.093 mmol) and triethylamine (21 μL; 0.150 mmol) are suspended in ethanol (6 mL). The reaction medium is held at 75° C. for 24 h. The solvent is evaporated off, and the crude product is washed with pentane and purified by flash chromatography, eluting with a mixture of dichloromethane and cyclohexane (2/1 by volume). This gives 34 mg (59%) of trans-diiodo(N-(L)valine methyl ester)[1-methyl-3-benzyl-imidazol-2-ylidene]platinum(II), represented by the following chemical structure,

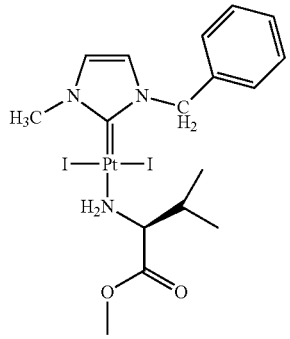

in the form of a yellow powder, which has the following characteristics:

$^1$H NMR spectrum (CDCl$_3$): δ 1.09 (d, 6H); 2.60 (m, 1H); 3.42 (m, 2H); 3.78 (s, 3H); 3.88 (s, 3H); 4.23 (m, 1H); 5.57 (s, 2H); 6.57 (d, 1H); 6.78 (d, 1H); 7.34-7.46 (m, 5H)

$^{13}$C NMR spectrum (CDCl$_3$): δ 17.9; 18.8; 29.7; 38.2; 52.4; 54.4; 63.7; 120.0; 122.3; 128.2; 128.5; 128.9; 135.3; 137.5; 172.8

Mass spectrum (positive ESI mode): calculated for C17H$_{25}$N$_3$I$_2$O$_2$PtNa: 774.96. found: 774.95.

ORTEP diagram shown below: obtained by X-ray diffraction. Crystals obtained from a solution in dichloromethane, by slow diffusion of pentane.

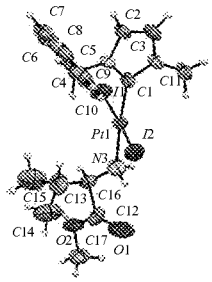

EXAMPLE 8 trans-diiodo(N-(L)-phenylalanine methyl ester)[1-methyl-3-benzyl-imidazol-2-ylidene]platinum(II)

The compound trans-diiodo(N-pyridine)[1-methyl-3-benzyl-imidazol-2-ylidene]platinum(II) (30 mg; 0.043 mmol), (L)-phenylalanine methyl ester hydrochloride (19 mg; 0.086 mmol) and triethylamine (23 μL; 0.171 mmol) are suspended in ethanol (2 mL). The reaction medium is held at 55° C. for 20 h. The solvent is evaporated off, and the crude product is washed with pentane and purified by flash chromatography, eluting with a mixture of dichloromethane and cyclohexane (2/1 by volume). This gives 24 mg (71%) of trans-diiodo(N-(L)phenylalanine methyl ester)[1-methyl-3-benzyl-imidazol-2-ylidene]platinum(II), represented by the following chemical structure,

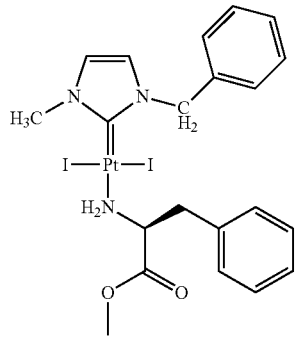

in the form of a yellow powder, which has the following characteristics:

$^1$H NMR spectrum (CDCl$_3$): δ 3.10-3.82 (m, 4H); 3.72 (s, 3H); 3.88 (s, 3H); 4.63 (m, 1H); 5.57 (s, 2H); 6.57 (d, 1H); 6.79 (d, 1H); 7.14-7.56 (m, 10H)

Mass spectrum (positive ESI mode): calculated for C$_{21}$H$_{25}$N$_3$I$_2$O$_2$PtNa: 822.96. found: 822.95.

EXAMPLE 9 trans-diiodo(N—[(S)-methyl-2-(2-amino-4-methyl-pentanamido)acetate])[1-methyl-3-benzyl-imidazol-2-ylidene]platinum(II)

The compound trans-diiodo(N-pyridine)[1-methyl-3-benzyl-imidazol-2-ylidene]platinum(II) (30 mg; 0.043 mmol), (L)Leu-Gly.OMe hydrotrifluoroacetate (27 mg; 0.086 mmol) and triethylamine (116 µL; 0.860 mmol) are suspended in ethanol (2 mL). The reaction medium is held at 55° C. for 20 h. The solvent is evaporated off, and the crude product is washed with pentane and purified by flash chromatography, eluting with dichloromethane. This gives 19 mg (54%) of trans-diiodo(N—(S)methyl-2-(2-amino-4-methylpentanamido)acetate) [1-methyl-3-benzyl-imidazol-2-ylidene]platinum(II), represented by the following chemical structure,

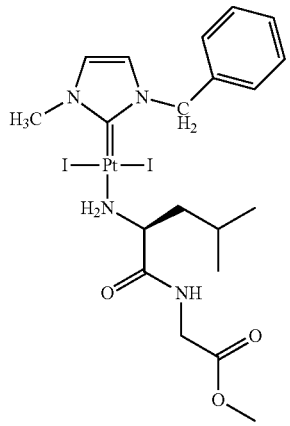

in the form of a yellow powder, which has the following characteristics:

$^1$H NMR spectrum (CD$_3$OD): δ 1.00 (m, 6H); 1.58-1.78 (m, 1H); 2.00-2.23 (m, 2H); 3.72 (s, 3H); 3.87 (s, 3H); 4.05-4.45 (m, 3H); 5.61 (s, 2H); 6.80 (d, 1H); 7.07 (d, 1H); 7.34 (m, 3H); 7.53 (m, 2H)

$^{13}$C NMR spectrum (CD$_3$OD): δ 21.4; 22.2; 24.5; 36.9; 40.5; 43.7; 51.2; 53.7; 57.0; 119.8; 122.4; 127.1; 128.2; 128.7; 136.1; 139.4; 170.2; 175.1

Mass spectrum (positive ESI mode): calculated for C$_{20}$H$_{30}$N$_4$I$_2$O$_3$PtNa: 846.00. found: 846.00.

EXAMPLE 10 trans-diiodo(N-[methyl 2-((R)-2-((R)-2-amino-3-methylbutanamido)-3-phenylpropanamido)acetate])[1-methyl-3-benzyl-imidazol-2-ylidene]platinum(II)

The compound trans-diiodo(N-pyridine)[1-methyl-3-benzyl-imidazol-2-ylidene]platinum(II) (20 mg; 0.029 mmol), (D)Val-(D)Phe-Gly.OMe hydrotrifluoroacetate (27 mg; 0.086 mmol) and triethylamine (15 µL; 0.114 mmol) are suspended in ethanol (1 mL). The reaction medium is held at 55° C. for 7 h. The solvent is evaporated off, and the crude product is washed with pentane and purified by flash chromatography, eluting with dichloromethane and then with a mixture of dichloromethane and methanol (20/1 by volume). This gives 7 mg (26%) of trans-diiodo(N-methyl 2-((R)-2-((R)-2-amino-3-methylbutanamido)-3-phenylpropanamido) acetate) [1-methyl-3-benzyl-imidazol-2-ylidene]platinum (II), represented by the following chemical structure,

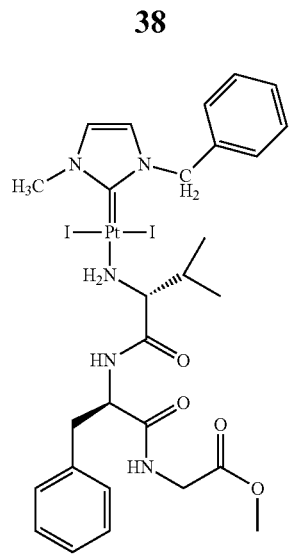

in the form of a yellow powder, which has the following characteristics:

$^1$H NMR spectrum (CDCl$_3$): δ 1.03 (m, 6H); 1.58-1.78 (m, 1H); 2.12-2.38 (m, 1H); 2.98-3.28 (m, 2H); 3.72 (s, 3H); 3.60-4.05 (m, 6H); 4.73 (m, 1H); 5.58 (d, 2H); 6.15 (t, 1H); 6.44 (d, 1H); 6.56 (d, 1H); 6.78 (d, 1H); 7.15-7.50 (m, 10H)

$^{13}$C NMR spectrum (CDCl$_3$): δ 18.4; 18.5; 32.0; 38.2; 38.5; 41.2; 52.4; 54.4; 54.9; 64.8; 119.9; 122.3; 127.1; 128.3; 128.8; 129.0; 129.4; 135.3; 136.2; 137.7; 169.4; 170.4; 170.7

Mass spectrum (positive ESI mode): calculated for C$_{28}$H$_{37}$N$_5$I$_2$O$_4$PtNa: 979.05. found: 979.05

ORTEP diagram shown below: obtained by X-ray diffraction. Crystals obtained from a solution in dichloromethane, by slow diffusion of diethyl ether (the hydrogens have been omitted for greater clarity).

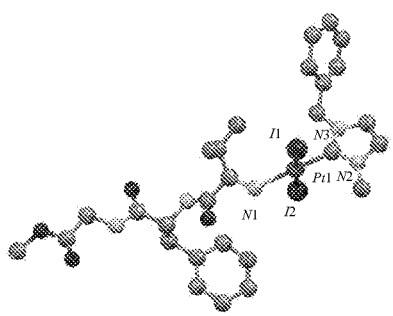

EXAMPLE 11 trans-diiodo(N-[methyl 2-((S)-2-((2S,3R)-2-amino-3-methylpentanamido)-6-((((2-chlorobenzyl)oxy)carbonyl)amino)hexanamido)acetate])[1-methyl-3-benzyl-imidazol-2-ylidene]platinum(II)

The compound trans-diiodo(N-pyridine)[1-methyl-3-benzyl-imidazol-2-ylidene]platinum(II) (20 mg; 0.029 mmol), (L)Ile-(L)Lys(Cl-Z)-Gly.OMe hydrotrifluoroacetate (32 mg; 0.052 mmol) and triethylamine (20 µL; 0.148 mmol) are suspended in methanol (1 mL). The reaction medium is held at 55° C. for 20 h. The solvent is evaporated off, and the crude product is washed with pentane and purified by flash chromatography, eluting with a mixture of dichloromethane and cyclohexane (1/1 by volume) and then with a mixture of dichloromethane and ethyl acetate (75/25 in volume). This gives 7 mg (20%) of trans-diiodo(N-methyl 2-((S)-2-((2S,3R)-2-amino-3-methylpentanamido)-6-((((2-chlorobenzyl)oxy)carbonyl)amino)hexanamido)acetate)[1-methyl-3-benzyl-imidazol-2-ylidene]platinum(II), represented by the following chemical structure,

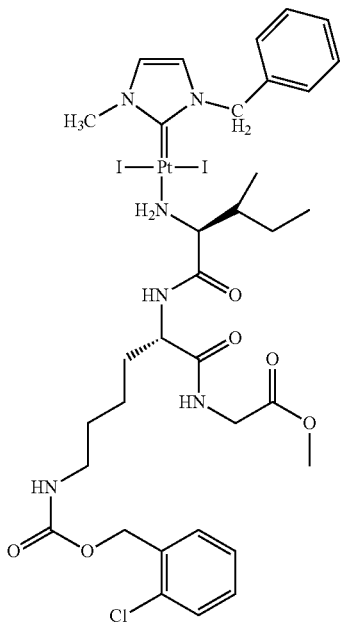

in the form of a yellow powder, which has the following characteristics:

$^1$H NMR spectrum (CDCl$_3$): δ 0.96-1.00 (m, 6H); 1.25-2.21 (m, 9H); 3.14-3.24 (m, 2H); 3.72 (s, 3H); 3.91 (s, 3H); 3.91-4.21 (m, 3H); 4.55 (m, 1H); 5.05 (t, 1H); 5.22 (s, 2H); 5.55 (d, 2H); 6.53 (d, 1H); 6.76 (d, 1H); 7.15-7.50 (m, 9H)

$^{13}$C NMR spectrum (CDCl$_3$): δ 11.7; 14.9; 22.2; 25.8; 29.3; 31.7; 38.1; 39.0; 40.3; 41.2; 52.4; 53.1; 54.3; 63.6; 63.9; 119.9; 122.3; 126.9; 128.3; 128.8; 129.1; 129.3; 129.5; 129.7; 133.4; 135.3; 137.9; 156.4; 169.9; 171.0

Mass spectrum (positive ESI mode): calculated for C$_{34}$H$_{47}$N$_6$I$_2$ClO$_6$PtNa: 1142.09; found: 1142.21

EXAMPLE 12 trans-diiodo(N-[(methoxy)polyethylene glycol amine])[1-methyl-3-benzyl-imidazol-2-ylidene]platinum(II)

The compound trans-diiodo(N-pyridine)[1-methyl-3-benzyl-imidazol-2-ylidene]platinum(II) (32 mg; 0.046 mmol) and (methoxy)polyethylene glycol amine (840 Da and D=1.04; 61 mg; 0.069 mmol) are suspended in ethanol (2 mL). The reaction medium is held at 55° C. for 20 h. The solvent is evaporated off, and the crude product is washed with pentane and purified by flash chromatography, eluting with a mixture of dichloromethane and methanol (10/1 by volume). This gives 30 mg (45%) of trans-diiodo(N-(methoxy)polyethylene glycol amine)[1-methyl-3-benzyl-imidazol-2-ylidene]platinum(II), represented by the following chemical structure,

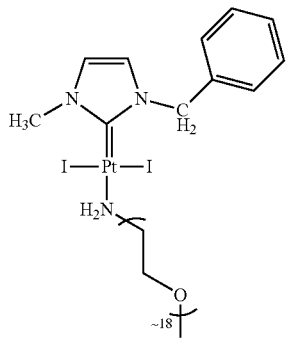

in the form of yellow oil, which has the following characteristics:

$^1$H NMR spectrum (CDCl$_3$): δ 2.05 (s, 2H); 3.18 (m, 4H); 3.37 (s, 3H); 3.40-3.79 (m, ~72H); 3.87 (s, 3H); 5.60 (s, 2H); 6.60 (d, 1H); 6.80 (d, 1H); 7.25-7.60 (m, 5H)

$^{13}$C NMR spectrum (CDCl$_3$): δ 38.1; 45.1; 54.4; 59.0; 70.2; 70.5; 71.9; 119.8; 122.2; 128.2; 128.8; 129.0; 135.4; 141.2.

EXAMPLE 13 trans-diiodo(N-[methyl-6-aminohexanoate])[1-methyl-3-benzyl-imidazol-2-ylidene]platinum(II)

The compound trans-diiodo(N-pyridine)[1-methyl-3-benzyl-imidazol-2-ylidene]platinum(II) (20 mg; 0.029 mmol) and methyl 6-aminohexanoate (13 mg; 0.090 mmol) are suspended in ethanol (2 mL). The reaction medium is held at 55° C. for 20 h. The solvent is evaporated off, and the crude product is washed with pentane and purified by flash chromatography, eluting with dichloromethane and then with a mixture of dichloromethane and methanol (20/1 by volume). This gives 10 mg (45%) of trans-diiodo(N-methyl-6-aminohexanoate)[1-methyl-3-benzyl-imidazol-2-ylidene]platinum(II), represented by the following chemical structure,

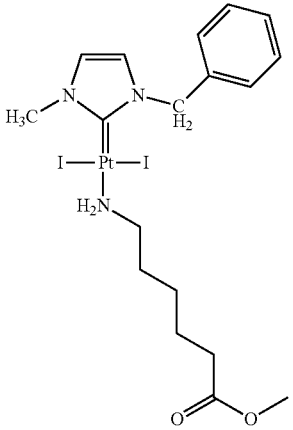

in the form of yellow oil, which has the following characteristics:

$^1$H NMR spectrum (CDCl$_3$): δ 1.26 (m, 2H); 1.66 (m, 4H); 2.33 (t, 2H); 3.04 (m, 4H); 3.66 (s, 3H); 3.89 (s, 3H); 5.59 (s, 2H); 6.57 (d, 1H); 6.78 (d, 1H); 7.32-7.46 (m, 5H)

$^{13}$C NMR spectrum (CDCl$_3$): δ 24.4; 26.0; 31.7; 33.8; 38.2; 45.3; 51.5; 54.4; 119.9; 122.2; 128.3; 128.8; 129.2; 135.4; 139.4; 173.8

Mass spectrum (positive ESI mode): calculated for $C_{18}H_{27}N_3I_2O_2PtNa$: 788.97. found: 788.97.

EXAMPLE 14 trans-diiodo(N-(L)-prolinol)[1-methyl-3-benzyl-imidazol-2-ylidene]platinum(II)

The compound trans-diiodo(N-pyridine)[1-methyl-3-benzyl-imidazol-2-ylidene]platinum(II) (31 mg; 0.044 mmol) and (L)-prolinol (13 µL; 0.131 mmol) are suspended in ethanol (2 mL). The reaction medium is held at 55° C. for 24 h. The solvent is evaporated off, and the crude product is washed with pentane and purified by flash chromatography, eluting with dichloromethane and then with a mixture of dichloromethane and methanol (20/1 by volume). This gives 28 mg (90%) of trans-diiodo(N-(L)-prolinol)[1-methyl-3-benzyl-imidazol-2-ylidene]platinum(II), represented by the following chemical structure,

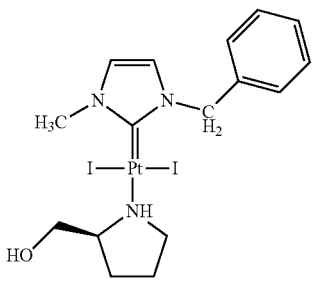

in the form of yellow oil, which has the following characteristics:

$^1$H NMR spectrum (CDCl$_3$): δ 1.73-1.86 (m, 4H); 2.36 (t, 1H); 3.12 (m, 1H); 3.24-3.68 (m, 4H); 3.89 (s, 3H); 4.45 (m, 1H); 5.58 (s, 2H); 6.57 (d, 1H); 6.79 (d, 1H); 7.32-7.46 (m, 5H)

$^{13}$C NMR spectrum (CDCl$_3$): δ 25.1; 26.4; 38.3; 52.1; 54.6; 60.3; 65.8; 120.2; 122.5; 128.6; 129.0; 129.2; 135.5; 139.3

Mass spectrum (positive ESI mode): calculated for $C_{16}H_{23}N_3I_2OPtNa$: 744.95. found: 744.96.

EXAMPLE 15 trans-diiodo(N-(L)-prolinamide)[1-methyl-3-benzyl-imidazol-2-ylidene]platinum(II)

The compound trans-diiodo(N-pyridine)[1-methyl-3-benzyl-imidazol-2-ylidene]platinum(II) (20 mg; 0.029 mmol), (L)-prolinamide hydrochloride (6 mg; 0.040 mmol) and triethylamine (20 µL; 0.148 mmol) are suspended in ethanol (1 mL). The reaction medium is held at 55° C. for 20 h. The solvent is evaporated off, and the crude product is washed with pentane and purified by flash chromatography, eluting with dichloromethane and then with a mixture of dichloromethane and methanol (20/1 by volume). This gives 8 mg (38%) of trans-diiodo(N-(L)-prolinamide) [1-methyl-3-benzyl-imidazol-2-ylidene]platinum(II), represented by the following chemical structure,

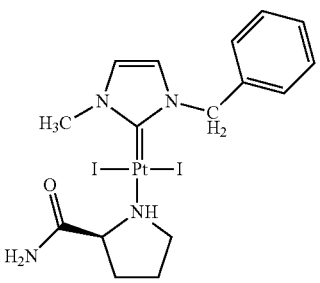

in the form of yellow oil, which has the following characteristics:

$^1$H NMR spectrum (CDCl$_3$): δ 1.73-2.20 (m, 4H); 3.26-3.40 (m, 2H); 3.87 (s, 3H); 4.41 (m, 1H); 4.52 (m, 1H); 5.58 (dd, 2H); 5.64 (m, 1H); 5.97 (m, 1H); 6.56 (s, 1H); 6.77 (s, 1H); 7.32-7.46 (m, 5H)

ORTEP diagram given below: obtained by X-ray diffraction. Crystals obtained from a solution in dichloromethane, by slow diffusion of pentane.

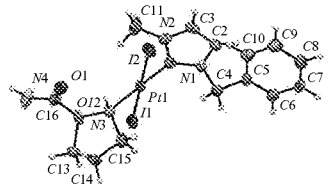

EXAMPLE 16 trans-diiodo(N-ethanolamine)[1-methyl-3-benzyl-imidazol-2-ylidene]platinum(II)

The compound trans-diiodo(N-pyridine) [1-methyl-3-benzyl-imidazol-2-ylidene]platinum(II) (20 mg; 0.029 mmol) and ethanolamine (9 µL; 0.143 mmol) are suspended in ethanol (1 mL). The reaction medium is held at 55° C. for 24 h. The solvent is evaporated off, and the crude product is washed with pentane and purified by flash chromatography, eluting with dichloromethane and then with a mixture of dichloromethane and methanol (20/1 by volume). This gives 16 mg (81%) of trans-diiodo(N-ethanolamine)[1-methyl-3-benzyl-imidazol-2-ylidene]platinum(II), represented by the following chemical structure,

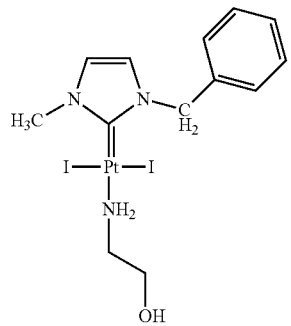

in the form of yellow oil, which has the following characteristics:

$^1$H NMR spectrum (CDCl$_3$): δ 2.50 (m, 1H); 3.16-3.25 (m, 4H); 3.89 (s, 3H); 3.99 (m, 2H); 5.59 (s, 2H); 6.59 (d, 1H); 6.80 (d, 1H); 7.32-7.46 (m, 5H)

$^{13}$C NMR spectrum (CDCl$_3$): δ 38.2; 47.2; 54.4; 60.8; 120.0; 122.3; 128.3; 138.7; 129.0; 135.3

EXAMPLE 17 trans-diiodo(N-[1-((2S,7S,12S,17S,22S)-22-amino-2,17-diisobutyl-12-isopropyl-7-methyl-4,9,14,19-tetraoxo-3,5,8,10,13,15,18,20-octaazatricosyl)-3-methylurea])[1-methyl-3-benzyl-imidazol-2-ylidene]platinum(II)

The compound trans-diiodo(N-pyridine)[1-methyl-3-benzyl-imidazol-2-ylidene]platinum(II) (19 mg; 0.026 mmol), (6S,11S,16S,21S,26S)-6,21-diisobutyl-16-isopropyl-11-methyl-3,8,13,18,23-pentaoxo-2,4,7,9,12,14,17,19,22,24-decaazaheptacosan-26-aminium chloride (18 mg; 0.026 mmol) and triethylamine (50 μL; 0.370 mmol) are suspended in ethanol (1 mL). The reaction medium is held at 55° C. for 24 h. The solvent is evaporated off, and the crude product is washed with pentane and purified by flash chromatography, eluting with dichloromethane and then with a mixture of dichloromethane and methanol (20/1 by volume). This gives 7 mg (21%) of trans-diiodo(N-[1-((2S,7S,12S,17S,22S)-22-amino-2,17-diisobutyl-12-isopropyl-7-methyl-4,9,14,19-tetraoxo-3,5,8,10,13,15,18,20-octaazatricosyl)-3-methylurea])[1-methyl-3-benzyl-imidazol-2-ylidene]platinum(II), represented by the following chemical structure,

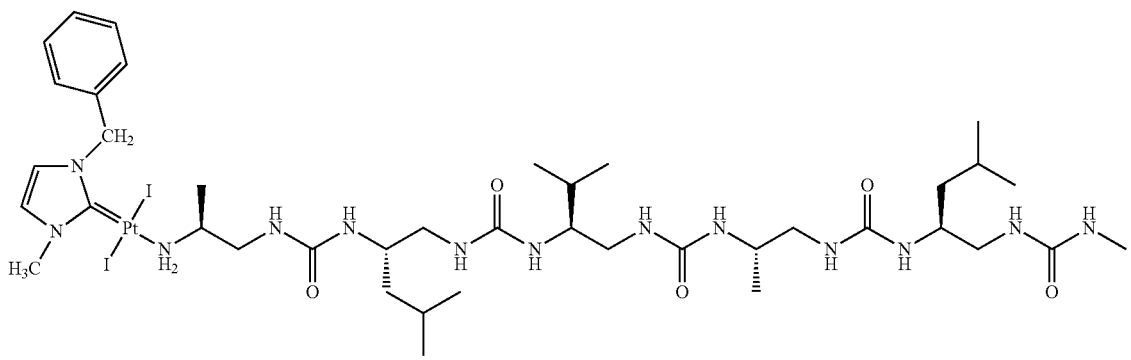

in the form of yellow oil, which has the following characteristics:

$^1$H NMR spectrum (CDCl$_3$): δ 0.84 (m, 18H); 1.01 (d, 3H); 1.21 (m, 4H); 1.35 (d, 3H); 1.50 (m, 1H); 1.68 (m, 2H); 2.10-2.50 (m, 3H); 2.66 (s, 3H), 2.83 (m, 10H); 3.00 (m, 2H); 3.52 (m, 4H); 3.83 (s, 3H); 3.84 (m, 3H); 5.40 (m, 1H); 5.52 (s, 2H); 5.62 (m, 1H); 5.70 (m, 2H); 6.05 (m, 1H); 6.32 (m, 1H); 6.53 (d, 1H); 6.77 (d, 1H); 7.27-7.41 (m, 5H)

EXAMPLE 18 trans-diiodo(N—[N,N-dimethyl-5-(piperazin-1-ylsulphonyl)naphthalen-1-amine])[1-methyl-3-benzyl-imidazol-2-ylidene]platinum(II)

Procedure 1:

The compound trans-diiodo(N-pyridine)[1-methyl-3-benzyl-imidazol-2-ylidene]platinum(II) (30 mg; 0.043 mmol) and N,N-dimethyl-5-(piperazin-1-ylsulphonyl)naphthalen-1-amine (18 mg; 0.056 mmol) are suspended in ethanol (2 mL). The reaction medium is held at 55° C. for 24 h. The solvent is evaporated off, and the crude product is washed with pentane and purified by flash chromatography, eluting with dichloromethane. This gives 28 mg (70%) of trans-diiodo(N—[N,N-dimethyl-5-(piperazin-1-ylsulphonyl)naphthalen-1-amine])[1-methyl-3-benzyl-imidazol-2-ylidene]platinum(II), represented by the following chemical structure,

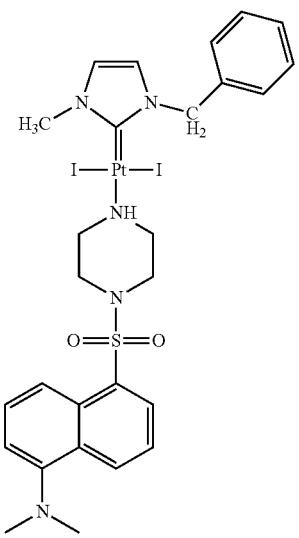

in the form of yellow oil.

Procedure 2:

The compound trans-diiodo(N-cyclohexylamine)[1-methyl-3-benzyl-imidazol-2-ylidene]platinum(II) (23 mg; 0.032 mmol) and N,N-dimethyl-5-(piperazin-1-ylsulphonyl)naphthalen-1-amine (13 mg; 0.042 mmol) are suspended in ethanol (2 mL). The reaction medium is held at 55° C. for 24 h. The solvent is evaporated off, and the crude product is washed with pentane and purified by flash chromatography, eluting with dichloromethane and then ethyl acetate. This gives 2 mg (6%) of trans-diiodo(N—[N,N-dimethyl-5-(piperazin-1-ylsulphonyl)naphthalen-1-amine]) [1-methyl-3-benzyl-imidazol-2-ylidene]platinum(II), in the form of yellow oil with the following characteristics:

$^1$H NMR spectrum (CDCl$_3$): δ 2.61 (m, 2H); 2.90 (s, 6H); 3.04 (m, 2H); 3.45 (m, 2H); 3.73 (m, 2H); 3.82 (s, 3H); 5.51 (s, 2H); 6.54 (d, 1H); 6.76 (d, 1H); 7.21 (d, 1H); 7.35 (m, 5H); 7.56 (dd, 2H); 8.19 (d, 1H); 8.37 (d, 1H); 8.60 (d, 1H)

EXAMPLE 19 trans-diiodo(N-phenylhydrazine)[1-methyl-3-benzyl-imidazol-2-ylidene]platinum(II)

The compound trans-diiodo(N-pyridine)[1-methyl-3-benzyl-imidazol-2-ylidene]platinum(II) (20 mg; 0.029 mmol) and phenylhydrazine (20 μL; 0.170 mmol) are suspended in ethanol (1 mL). The reaction medium is held at 55° C. for 24 h. The solvent is evaporated off, and the crude product is washed with pentane and purified by flash chromatography, eluting with dichloromethane. This gives 17 mg (81%) of trans-diiodo(N-phenylhydrazine)[1-methyl-3-benzyl-imidazol-2-ylidene]platinum(II), represented by the following chemical structure,

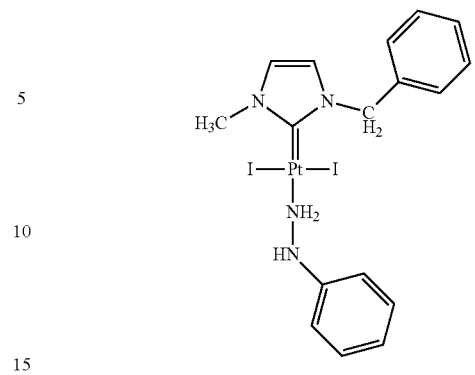

in the form of a yellow solid, which has the following characteristics:

$^1$H NMR spectrum (CDCl$_3$): δ 3.90 (s, 3H); 5.06 (m, 2H); 5.60 (s, 2H); 6.30 (m, 1H); 6.54 (d, 1H); 6.61 (d, 1H); 6.85 (d, 2H); 6.99 (t, 1H); 7.29-7.46 (m, 7H)

EXAMPLE 20 trans-diiodo(N-diethylenetriamine)[1-methyl-3-benzyl-imidazol-2-ylidene]platinum(II)

The compound trans-diiodo(N-pyridine)[1-methyl-3-benzyl-imidazol-2-ylidene]platinum(II) (10 mg; 0.014 mmol) and diethylenetriamine (8 μL; 0.072 mmol) are suspended in ethanol (2 mL). The reaction medium is held at 55° C. for 3 h. The crude reaction product is filtered on Celite and the filtrate is concentrated, washed with dichloromethane and with THF. This gives 6 mg (60%) of iodo(N,N'-diethylenetriamine)[1-methyl-3-benzyl-imidazol-2-ylidene]platinum(II) iodide, illustrated below:

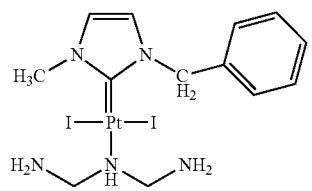

in the form of a white solid, which has the following characteristics:

$^1$H NMR spectrum (CD$_3$CN): δ 2.50-3.20 (m, 8H); 3.55-3.86 (m, 2H); 3.95 and 4.03 (s, 3H); 5.55 (s, 2H); 7.00-7.61 (m, 7H)

$^{13}$C NMR spectrum (DMSO-d$_6$): δ 38.0; 38.1; 51.3; 51.5; 51.6; 51.8; 53.7; 54.0; 122.0; 124.0; 128.7; 129.1; 129.3; 129.4; 136.7; 137.1; 149.6; 149.9

Mass spectrum (positive ESI mode): calculated for C15H$_{25}$N$_5$IPt: 597.08. found: 597.08

ORTEP diagram given below: obtained by X-ray diffraction. Crystals obtained from a solution in acetonitrile, by diffusion of ether vapour.

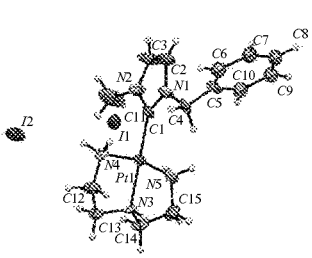

EXAMPLE 21 trans-diiodo(N-ethylenediamine)[1-methyl-3-benzyl-imidazol-2-ylidene]platinum(II)

The compound trans-diiodo(N-pyridine)[1-methyl-3-benzyl-imidazol-2-ylidene]platinum(II) (20 mg; 0.029 mmol) and ethylenediamine (10 µL; 0.143 mmol) are suspended in ethanol (1.5 mL). The reaction medium is held at 55° C. for 20 h. The crude reaction product is filtered on Celite and the filtrate is concentrated, washed with dichloromethane and with pentane. This gives 10 mg (50%) of iodo(N,N'-ethylenediamine)[1-methyl-3-benzyl-imidazol-2-ylidene]platinum(II) iodide, illustrated below:

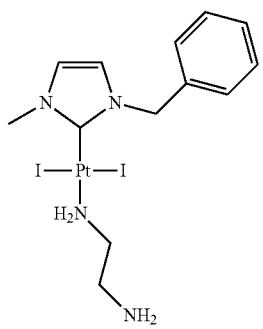

in the form of a white solid, which has the following characteristics:

$^1$H NMR spectrum (DMSO-$d_6$): δ 2.20-2.60 (m, 4H); 3.83 (s, 3H); 5.00 (s, 2H); 5.05-5.85 (dd, 2H); 7.10 (s, 1H); 7.30-7.45 (m, 6H).

A mixture of two isomers of iodo(N,N'-ethylenediamine)[1-methyl-3-benzyl-imidazol-2-ylidene]platinum(II) iodide is obtained under the experimental conditions. The two isomers are illustrated below.

EXAMPLE 22 trans-diiodo(N-poly(ethylenamine))[1-methyl-3-benzyl-imidazol-2-ylidene]platinum(II)

The compound trans-diiodo(N-pyridine)[1-methyl-3-benzyl-imidazol-2-ylidene]platinum(II) (20 mg; 0.029 mmol) and linear poly(ethylenamine) (~21532 Da; 13 mg; 0.557 µmol) are suspended in ethanol (2 mL). The reaction medium is held at 55° C. for 24 h. The crude reaction product is filtered on Celite and the filtrate is concentrated, and washed with dichloromethane. This gives 28 mg of iodo(N,N'-poly(ethylenimine))[1-methyl-3-benzyl-imidazol-2-ylidene]platinum(II) iodide, illustrated below:

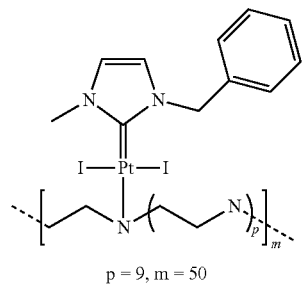

p = 9, m = 50 in the form of a white solid, which has the following characteristics:

$^1$H NMR spectrum (2:1 mixture CD$_3$CN and CD$_3$OD): δ 2.15-3.75 (m, 71H); 4.05-4.45 (m, 3H); 5.85 (m, 2H); 7.10-7.95 (m, 7H); experimental ratio determined by $^1$H NMR: 1 Pt/14 NH.

$^{13}$C NMR spectrum (2:1 mixture CD$_3$CN and CD$_3$OD): δ 38.8; 46.2; 48.4-59.6; 122.2-125.0; 128.9-130.7; 136.4-138.9; 153.2-155.4

EXAMPLE 23 trans-diiodo(N-[16β-hydroxymethyl-16α-(aminoalkyl)-1,3,5(10)-estratriene-3,17-diol])[1-methyl-3-benzyl-imidazol-2-ylidene]platinum(II)

The compound trans-diiodo(N-pyridine) [1-methyl-3-benzyl-imidazol-2-ylidene]platinum(II) (20 mg; 0.029 mmol), estradiol derivative: (13S,16R,17R)-16-(7-aminoheptyl)-16-(hydroxymethyl)-13-methyl-7,8,9,11,12,13,14,15,16,17-decahydro-6H-cyclopenta[α]phenanthrene-3,17-diol (22 mg; 0.05 mmol) are suspended in methanol (1 mL). The reaction medium is held at 55° C. for 20 h. The solvent is evaporated off, and the crude product is washed with pentane and purified by flash chromatography, eluting with a mixture of dichloromethane and cyclohexane and then with a mixture of dichloromethane and ethyl acetate. This gives the compound represented by the following chemical structure:

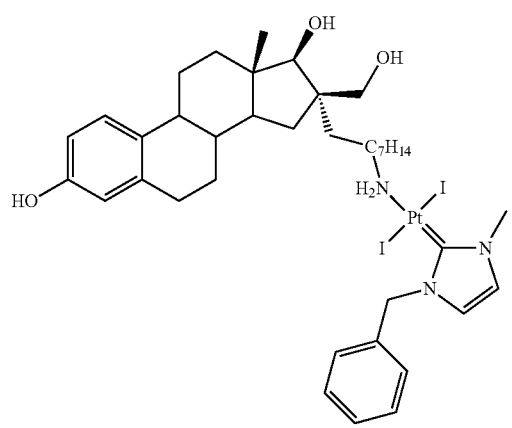

EXAMPLE 24 trans-diiodo(N-[16β-hydroxymethyl-16-(amino[polyethyleneglycol])-1,3,5 (10)-estratriene-3,17-diol])[1-methyl-3-benzyl-imidazol-2-ylidene]platinum(II)

The compound trans-diiodo(N-pyridine)[1-methyl-3-benzyl-imidazol-2-ylidene]platinum(II) (20 mg; 0.029 mmol), estradiol derivative: 16β-hydroxymethyl-16-(amino[polyethyleneglycol])-1,3,5(10)-estratriene-3,17-diol (26 mg; 0.05 mmol) are suspended in methanol (1 mL). The reaction medium is held at 55° C. for 20 h. The solvent is evaporated off, and the crude product is washed with pentane and purified by flash chromatography, eluting with a mixture of dichloromethane and cyclohexane and then with a mixture of dichloromethane and ethyl acetate. This gives the compound represented by the following chemical structure:

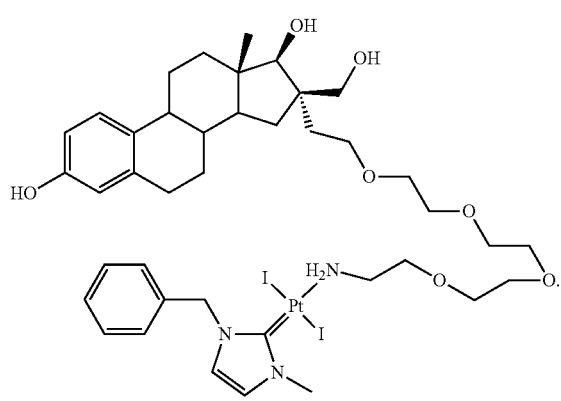

EXAMPLE 25

Platinum Carbene/Heterodimeric Inhibitor of PMSA (Prostate Specific Membrane Antigen) Conjugate

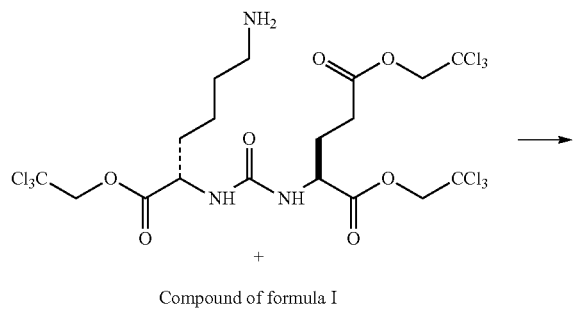

Compound of formula I
+

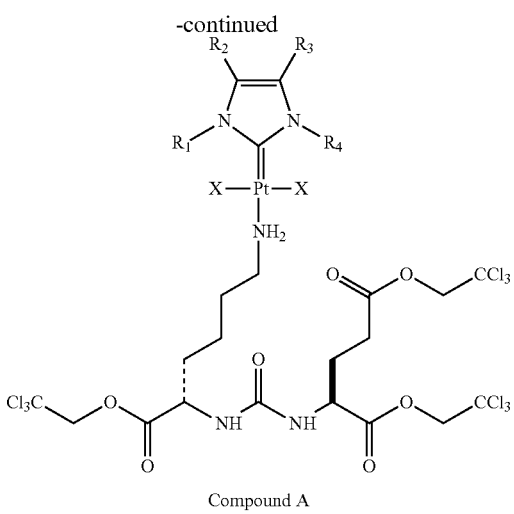

Compound A

Compound I is synthesized under the standard conditions described in the literature (*J. Med. Chem.* 2009, 52, 347-357).

The lysine amine is then reacted with a platinum precursor complex NHC of formula I, to give compound A.

The 2,2,2-trichloroethyl ester group can be deprotected by treatment with zinc to give compound B shown below.

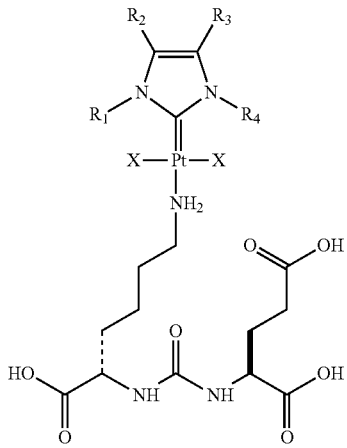

Compound B

EXAMPLE 26

Platinum Carbene—Cyclo(RGDfK) Cyclic Peptide Conjugate

The cyclo(RGDfK) peptide displays high affinity for integrin αvβ3, which plays an important role in angiogenesis and tumour cell metastasis.

The linear peptide, having the amino acid sequence H-Arg (HCl)-Gly-Asp($CH_2Cl_3$)-D-Phe-Lys($N_3$)—OH, is the precursor peptide of the cyclo(RGDfK) peptide.

Synthesis of the partially protected linear peptide is carried out under the standard conditions of supported peptide synthesis starting from a 2-chlorotrityl polystyrene chloride resin, on which the amino acid Fmoc-Lys(N3)-OH is grafted. A succession of steps of deprotection (piperidine, DMF) and then coupling (BOP, DIEA, DMF) leads to the resin peptide having the sequence Boc Arg-H)ClGly-(AspO)CH$_2$Cl$_3$D-(Phe-LysN3)(-. Treatment with trifluoroacetic acid leads to the linear peptide precursor of the cyclo(RGDfK) peptide.

Cyclization of the precursor peptide of cyclo(RGDfK), carried out by treatment with BOP and DIEA in DMF according to the conditions described by Reid et al. (*J. Org. Chem.* 2003, 68, 4464-4471), gives the cyclo(RGDfK) peptide, illustrated by the following chemical structure:

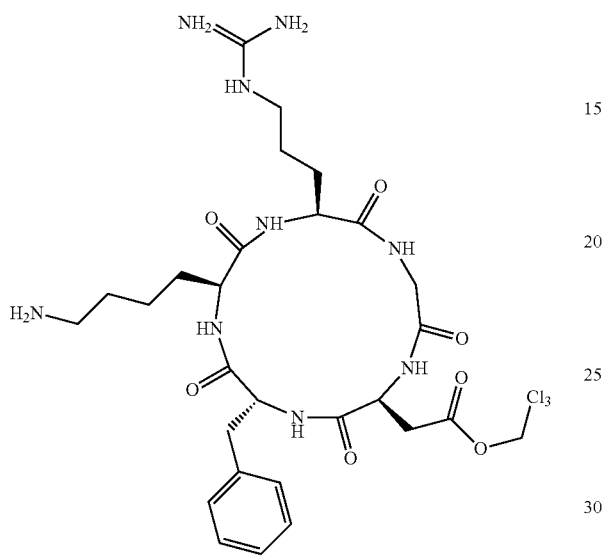

After reduction of the nitride function (H$_2$, Pd/C), the amide of the lysine of the cyclo(RGDfK) peptide is then reacted with a platinum precursor complex NHC of formula I to give compound C. This reaction is presented below:

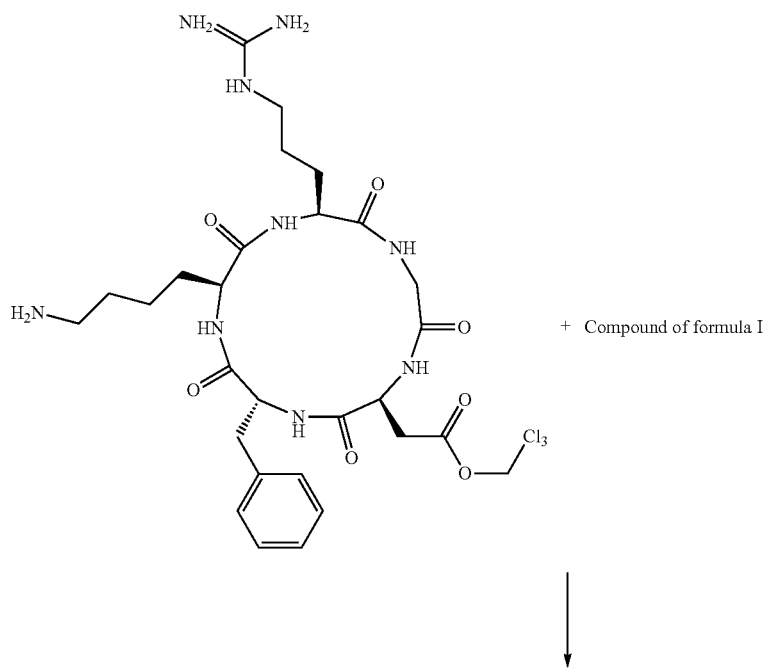

+ Compound of formula I

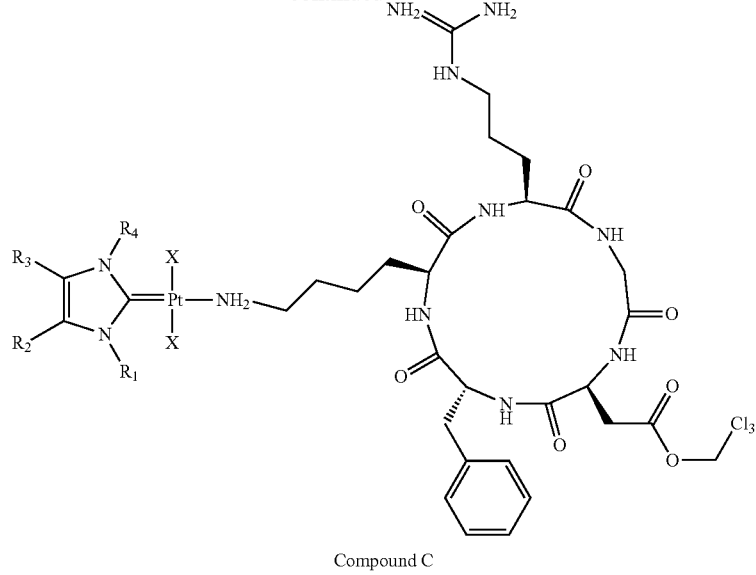
Compound C
The ester group of 2,2,2-trichloroethyl can be deprotected by treatment with zinc to give compound D shown below.
Compound D
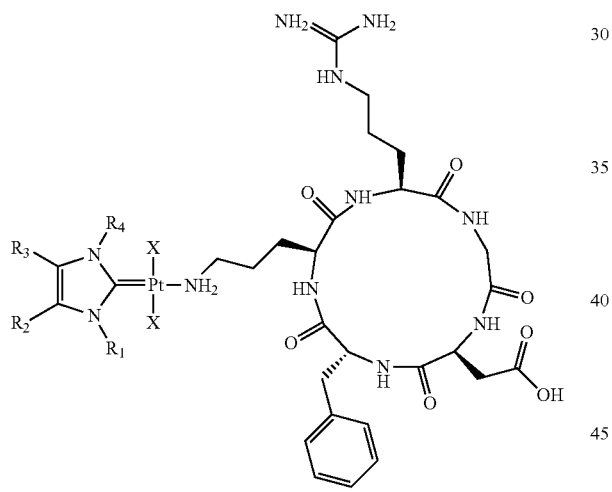
EXAMPLE 27 (COMPARATIVE)
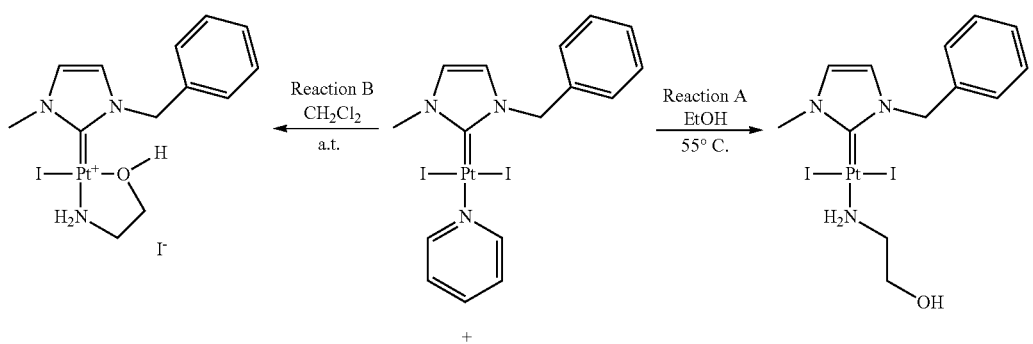

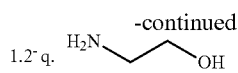

When the compound trans-diiodo(N-pyridine)[1-methyl-3-benzyl-imidazol-2-ylidene]platinum(II) (20 mg; 0.029 mmol) and ethanolamine (9 µL; 0.143 mmol) are suspended in ethanol (1 mL), at 55° C. for 24 h, in the experimental conditions as described in Example 16, trans-diiodo(N-ethanolamine)[1-methyl-3-benzyl-imidazol-2-ylidene]platinum(II) is obtained. (see above, reaction A)

Conversely, when the compound trans-diiodo(N-pyridine)[1-methyl-3-benzyl-imidazole-imidazol-2-ylidene]platinum(II) (20 mg; 0.029 mmol) and ethanolamine (9 µL; 0.143 mmol) are suspended in CH₂Cl₂, at room temperature, only the following product is obtained:

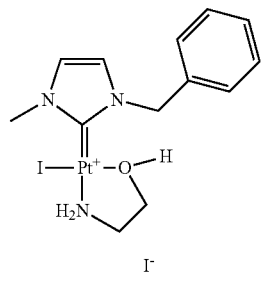

(see above, reaction B).

EXAMPLE 28 (COMPARATIVE)

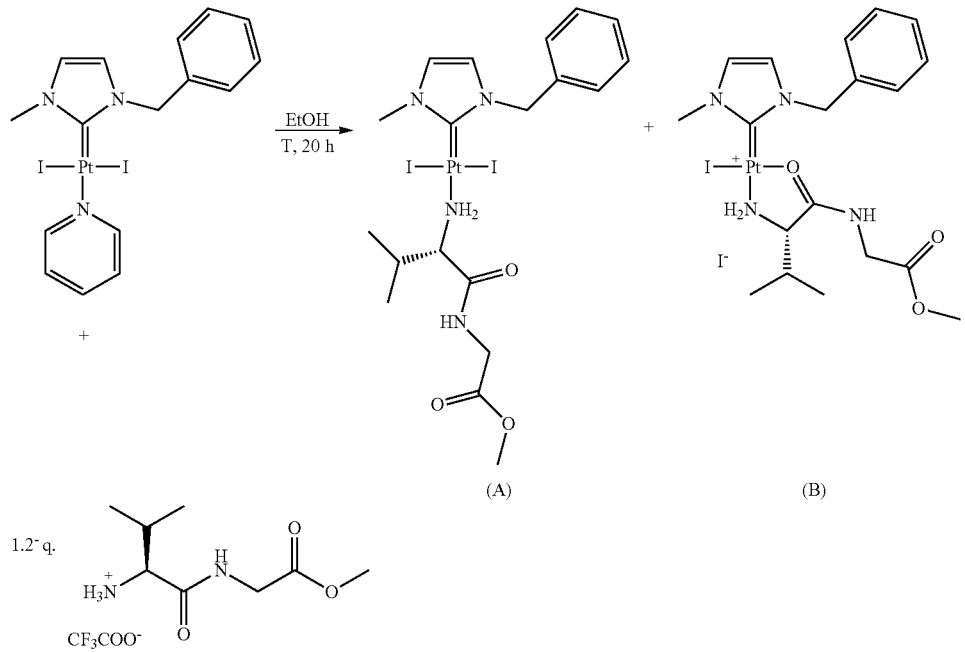

When the compound trans-diiodo(N-pyridine)[1-methyl-3-benzyl-imidazole-imidazol-2-ylidene]platinum(II) (30 mg; 0.043 mmol), (L)Leu-Gly.OMe hydrotrifluoroacetate (27 mg; 0.086 mmol) and triethylamine (116 µL; 0.860 mmol) are suspended in ethanol (2 mL), at 55° C. for 20 h, only trans-diiodo(N—(S)methyl-2-(2-amino-4-methylpentanamido)acetate)[1-methyl-3-benzyl-imidazole-imidazol-2-ylidene]platinum(II) is obtained (product A, shown above).

Conversely, when the reaction medium containing the two aforementioned compounds is held at 75° C., a mixture of product A and product B is obtained (shown above).

The invention claimed is:

1. A process for preparing platinum-carbene complexes of the following formula II:

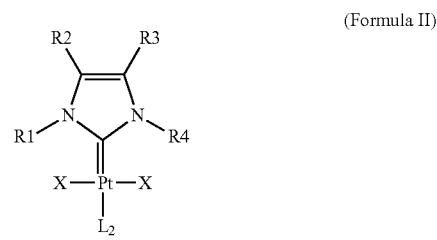

(Formula II)

in which:
R1 and R4 represent, independently of one another:
(i) a linear or branched C1-C12 alkyl group, optionally substituted with an alkoxy group with 1 to 12 carbon atoms, with a CF₃ group or with a trimethylsilyl group,
(ii) a linear or branched C2-C12 alkenyl group, optionally substituted with an alkyl group with 1 to 12 carbon atoms, with an alkoxy group with 1 to 12 carbon atoms, with a CF₃ group or with a trimethylsilyl group,
(iii) a linear or branched C2-C12 alkynyl group, optionally substituted with an alkyl group with 1 to 12 carbon atoms, with an alkoxy group with 1 to 12 carbon atoms, with a $CF_3$ group or with a trimethylsilyl group,
(iv) an aryl group having 1, 2 or 3 aromatic rings or aralkyl with a C1-C12 carbon chain, the aryl or aralkyl group being optionally substituted with a C1-C12 alkyl group, or with a C1-C12 alkoxy group, with a $CF_3$ group, or with a trimethylsilyl group,
(v) a C3-C7 cycloalkyl, optionally substituted with an alkyl group with 1 to 12 carbon atoms, with an alkoxy group with 1 to carbon atoms, with a $CF_3$ group, or with a trimethylsilyl group, or
(vi) a polymer represented by the formula $—(CH_2CH_2O)_n—R'$ or a polymer represented by the formula $—(CH_2CH_2CH_2O)_n—R'$, in which n=1 to 40, and R' is a C1-C12 alkyl group,
R2 and R3 represent, independently of one another:
a hydrogen,
an aryl or aralkyl group, or
a linear or branched C2-C12 alkynyl group, optionally substituted with an alkyl group with 1 to 12 carbon atoms, with an alkoxy group with 1 to 12 carbon atoms, with a $CF_3$ group, or with a trimethylsilyl group,
X represents iodine, bromine or chlorine,
$L_2$ represent:
(i) an amine of formula

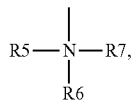

in which R5, R6 and R7 represent, independently of one another:
(a) a hydrogen,
(b) a linear or branched C1-C18 alkyl, optionally substituted with an estradiol,
(c) an aryl group having 1, 2 or 3 aromatic rings, or aralkyl with a C1-C12 carbon chain, the aryl or aralkyl group being optionally substituted with a C1-C12 alkoxy group, or an alkyl group with 1 to 12 carbon atoms, with a $CF_3$ group or with a trimethylsilyl group,
(d) a C3-C7 cycloalkyl, optionally substituted with an alkyl group with 1 to 12 carbon atoms, with an alkoxy group with 1 to 12 carbon atoms, with a $CF_3$ group, or with a trimethylsilyl,
(e) a polymer represented by the formula $—(CH_2CH_2O)_n—R'$ or the formula $—(CH_2CH_2CH_2O)_n—R'$, in which n=1 to 40, and R' is a C1-C12 alkyl group, optionally substituted with an estradiol,
(ii) a diamine of general formula $NH_2—(CH_2)_n—NH_2$, n=1 to 12 carbon atoms,
(iii) a triamine of general formula $NH_2—(CH_2)_n—NH—(CH_2)_m—NH_2$, n=1 to 12 carbon atoms, m=1 to 12 carbon atoms,
(iv) a linear or branched amino alcohol with 2 to 20 carbon atoms, (v) a linear or branched amino ester with 2 to 20 carbon atoms,
(vi) a linear or branched amino amide with 2 to 20 carbon atoms,
(vii) an amino acid or esters or amides thereof,
(viii) a beta or gamma amino acid or its esters or amides,
(ix) a peptide, optionally cyclic, comprising 2 to 30 amino acids,
(x) a morpholine,
(xi) a piperazine optionally substituted with an alkyl group with 1 to 12 carbon atoms, with an alkoxy group with 1 to 12 carbon atoms, with a $CF_3$ group, or with a trimethylsilyl,
(xii) a piperazine N-substituted with a dansyl or dabsyl group
(xiii) a hydrazine monosubstituted with an aryl having 1, 2 or 3 aromatic rings, or a linear or branched alkyl with 1 to 12 carbon atoms,
(xiv) a glucamine optionally N-substituted with an alkyl group with 1 to 20 carbon atoms, (xv) a glucosamine optionally N-substituted with an alkyl group with 1 to 20 carbon atoms,
(xvi) a pseudopeptide of general formula $H—(NH—CH(R)—CH_2—X—CO)_n—NHR''$, with R being a side chain of one of the 20 proteinogenic amino acids; X being independently, throughout the sequence, $CH_2$, O or NH; n=1-15; R''=H, or a short alkyl or aralkyl chain,
(xvii) a pseudopeptide of general formula $R_a—CO—CH(R_b)—NH—CO—NH—CH(R_c)—CO—R_d$ in which $R_a$ and $R_d$ represent, independently of one another, H, a linear or branched C1-C6 alkyl group, a C3-C7 monocyclic cycloalkyl group, or a carboxylic acid protective group; $R_b$ represents the side chain of lysine, the amine of said side chain being optionally substituted with a group $—CO—(CH_2)_5—NH_2$; $R_c$ represents a side chain of one of the 20 proteinogenic amino acids, optionally protected by an protective group,
(xviii) a polymer represented by the general formula $NH_2—(CH_2(CH_2)_iNH)_{(n-1)}—H$, in which i=1, 2 or 3, n=1 to 1000, said polymer forming m coordination bonds with m platinum atoms, one of said coordination bonds being formed between Pt and $L_2$ of formula (II) and m-1 coordination bonds being formed with m-1 groups of formula 1:

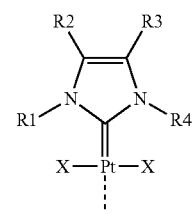

where $R_1$, $R_2$, $R_3$, $R_4$ and X are as defined above,
the number m being between 1 and n, the ratio m/n representing the number of platinum atoms to the number of amines of type —NH— or $—NH_2$, said process comprising reaction of the compound of formula I:

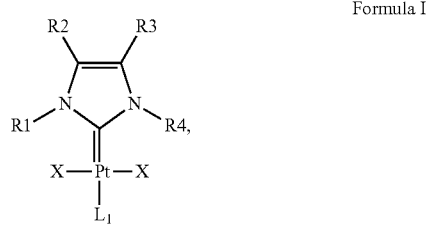

Formula I in which:
R1, R2, R3, R4 and X have the meanings given above,

L₁ representing a pyridine, or a pyridine substituted with iodine, bromine or chlorine, or disubstituted with iodine, bromine or chlorine, with a ligand L₂, or a salt of a ligand L₂, said reaction being carried out optionally in the presence of a solvent.

2. The process according to claim 1, wherein said reaction is carried out in the presence of a solvent selected from the group consisting of ethanol, methanol, dichloromethane, tetrahydrofuran, toluene, and ethyl acetate.

3. The process according to claim 1, wherein said reaction is carried out in the absence of solvent, L₂ being liquid at the reaction temperature and performing the role of solvent.

4. The process according to claim 1, comprising adding a base selected from a tertiary amine, when the ligand L₂ is in the form of salt.

5. The process according to claim 1, wherein said compound of formula I is reacted with a salt of a ligand L₂, said salt being in the form of ammonium salt, to obtain a compound of formula (II), wherein L₂ is an amine.

6. The process according to claim 1, wherein the temperature of the reaction is from 10° C. to 65° C.

7. The process according to claim 1, wherein the reaction between the compound of formula I and the ligand L₂ is carried out in the presence of ethanol as solvent, at a temperature from 45° C. to 65° C.

8. The process according to claim 1, wherein the reaction between the compound of formula I and the ligand L₂ is carried out in the presence of dichloromethane as solvent, at a temperature from 10° C. to 35° C.

9. The process for preparing the platinum-carbene complexes of formula II according to claim 1, in which the compound of formula I is obtained by reacting (i) a compound of formula III:

Formula III

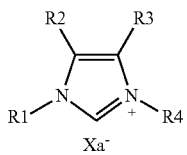

in which:
(a) R1, R2, R3, R4 have the meanings given above,
(b) Xa represents iodine, bromine or chlorine, or a counteranion,
with the following molecules:
(ii) Pt(Xb)₂, in which Xb represents iodine, bromine or chlorine, and
(iii) a ligand L₁, L₁ representing a pyridine, a pyridine substituted with iodine, bromine or chlorine, or disubstituted with iodine, bromine or chlorine, and
(iv) optionally NaXc in excess relative to Xa or to Xb, Xc representing iodine, bromine or chlorine,
said reaction being carried out optionally in the presence of a solvent.

10. The process according to claim 9, wherein said reaction is carried out without solvent, the ligand L₁ being liquid at the reaction temperature.

11. The process according to claim 9, wherein the process is carried out with NaXc in excess with respect to Xa and Xb, when Xa is different from Xb.

12. The process according to claim 9, wherein the process is optionally without the addition of NaXc, when Xa and Xb are identical.

13. The process according to claim 9, wherein the reaction between the compound of formula III and the ligand L₁ is carried out in the presence of a base.

14. A process according to claim 1, for preparing platinum-carbene complexes of the following formula II:

(Formula II)

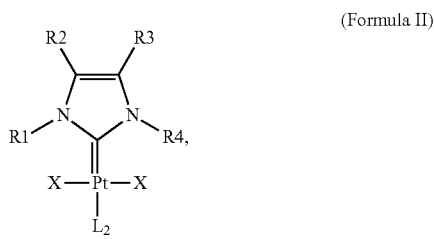

in which:
R1 and R4 represent, independently of one another:
(i) a linear or branched C1-C8 alkyl group, optionally substituted with an alkoxy group with 1 to 8 carbon atoms, with a CF₃ group or with a trimethylsilyl group,
(ii) a linear or branched C2-C8 alkenyl group, optionally substituted with an alkyl group with 1 to 12 carbon atoms, with an alkoxy group with 1 to 8 carbon atoms, with a CF₃ group, or with a trimethylsilyl group,
(iii) a linear or branched C2-C8 alkynyl group, optionally substituted with an alkyl group with 1 to 12 carbon atoms, with an alkoxy group with 1 to 8 carbon atoms, with a CF₃ group, or with a trimethylsilyl group,
(iv) a phenyl or aralkyl with a C1-C8 carbon chain, the phenyl or aralkyl group being optionally substituted with a C1-C8 alkyl group, or with a methoxy, with a CF₃ group or with a trimethylsilyl group,
(v) a C3-C7 cycloalkyl, optionally substituted with an alkyl group with 1 to 8 carbon atoms, with an alkoxy group with 1 to 8 carbon atoms, with a CF₃ group, or with a trimethylsilyl group, or
(vi) a polymer represented by the formula —(CH₂CH₂O)ₙ—R' or a polymer represented by the formula —(CH₂CH₂CH₂O)ₙ—R', in which n=1 to 20, and R' is a C1-C8 alkyl group,
R2 and R3 represent, independently of one another:
a hydrogen,
a phenyl or benzyl group, or
a linear or branched C2-C8 alkynyl group, optionally substituted with an alkyl group with 1 to 8 carbon atoms, with an alkoxy group with 1 to 8 carbon atoms, with a CF₃ group, or with a trimethylsilyl group,
X represents iodine, bromine or chlorine,
L₂ represent:
(i) an amine of formula

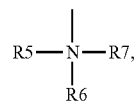

in which R5, R6 and R7 represent, independently of one another:
(a) a hydrogen,
(b) a linear or branched C1-C18 alkyl, optionally substituted with an estradiol,
(c) a phenyl, or aralkyl with a C1-C8 carbon chain, the phenyl, aralkyl group being optionally substituted with a methoxy, or an alkyl group with 1 to 8 carbon atoms, with a CF$_3$ group or with a trimethylsilyl group, (d) a C3-C7 cycloalkyl, optionally substituted with an alkyl group with 1 to 8 carbon atoms, with an alkoxy group with 1 to 8 carbon atoms, with a CF$_3$ group, or with a trimethylsilyl, (e) a polymer represented by the formula —(CH$_2$CH$_2$O)$_n$—R' or by the formula —(CH$_2$CH$_2$CH$_2$O)$_n$—R', in which n=1 to 20, and R' is a C1-C8 alkyl group, optionally substituted with an estradiol, (ii) a diamine of general formula NH$_2$—(CH$_2$)$_n$—NH$_2$, n=1 to 12 carbon atoms, (iii) a triamine of general formula NH$_2$—(CH$_2$)$_n$—NH—(CH$_2$)$_m$—NH$_2$, n=1 to 12 carbon atoms, m=1 to 12 carbon atoms, (iv) prolinol, (v) a linear or branched amino ester with 2 to 10 carbon atoms, (vi) prolinamide, (vii) an amino acid selected from the 20 proteinogenic α-amino acids or their esters or amides, (viii) a beta or gamma amino acid or its esters or amides, (ix) a peptide, optionally cyclic, comprising 2 to 10 amino acids, (x) a morpholine, (xi) a piperazine optionally substituted with an alkyl group with 1 to 8 carbon atoms, with an alkoxy group with 1 1 to 8 carbon atoms, with a CF$_3$ group, or with a trimethylsilyl group, (xii) a piperazine N-substituted with a dansyl or dabsyl group, (xiii) a hydrazine monosubstituted with a phenyl, or a linear or branched alkyl with 1 to 12 carbon atoms, (xiv) N-methylglucamine, N-ethylglucamine or N-dodecylglucamine, (xv) a glucosamine optionally N-substituted with an alkyl group with 1 to 20 carbon atoms, or (xvi) a pseudopeptide of general formula H—(NH—CH(R)—CH$_2$—X—CO)$_n$—NHR", with R being a side chain of one of the 20 proteinogenic amino acids; X being independently, throughout the sequence, CH$_2$, O or NH; n=1-15; R"=H, or a short alkyl or aralkyl chain, (xvii) a pseudopeptide of general formula R$_a$—CO—CH(R$_b$)—NH—CO—NH—CH(R$_c$)—CO—R$_d$ in which R$_a$ and R$_d$ represent, independently of one another, H, a linear or branched C1-C6 alkyl group, a C3-C7 monocyclic cycloalkyl group, or a carboxylic acid protective group; R$_b$ represents the side chain of lysine, the amine of said side chain being optionally substituted with a group —CO—(CH$_2$)$_5$—NH$_2$; R$_c$ represents a side chain of one of the 20 proteinogenic amino acids, optionally protected by an ad hoc protective group, (xviii) a polymer represented by the general formula NH$_2$—(CH$_2$(CH$_2$)$_i$NH)$_{(n-1)}$—H, in which i=1, 2 or 3, n=1 to 500, said polymer forming m coordination bonds with m platinum atoms, one of said coordination bonds being formed between Pt and L$_2$ of formula (II) and m-1 coordination bonds being formed with m-1 groups of formula 1:

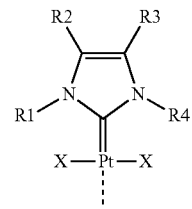

where R$_1$, R$_2$, R$_3$, R$_4$ and X are as defined above, the number m being between 1 and n, the ratio m/n representing the number of platinum atoms to the number of amines of type —NH— or —NH$_2$, said process comprising:

(i) reacting a compound of the following formula III:

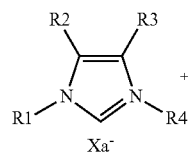

Formula III in which:

(a) R1, R2, R3, R4 have the meanings given above, (b) Xa represents iodine, bromine or chlorine, with Pt(Xb)$_2$, and a ligand L$_1$ and optionally NaXc in excess, to obtain a compound of the following formula I

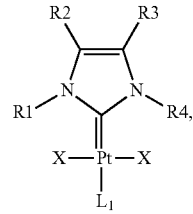

Formula I in which

R1, R2, R3, R4 and X have the meanings given above,

L$_1$ representing 3-bromopyridine, or 3-chloropyridine, or 3,5-dibromopyridine, and (ii) reacting the compound of formula I above with a ligand L$_2$, carried out optionally in the presence of a solvent, to obtain a platinum-carbene complex of formula II above.

15. The process according to claim 1, wherein, (A) L$_2$ represents:

(i) an amine of formula

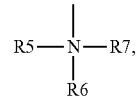

in which R5, R6 and R7 represent, independently of one another:

(b) a linear or branched, non-cyclized C1-C18 alkyl, optionally substituted with an estradiol, (c) an aryl having 1 or 2 or 3 aromatic rings, optionally substituted with a C1-C12 alkoxy group, or with an alkyl group with 1 to 12 carbon atoms, with a $CF_3$ group or with a trimethylsilyl, (d) a polymer represented by the formula $—(CH_2CH_2O)_n—R'$ or the formula $—(CH_2CH_2CH_2O)_n—R'$, in which n=1 to 40, and R' is a C1-C12 C1-C8 alkyl group, optionally substituted with an estradiol, provided that at least one of the R5, R6 and R7 radicals is different from hydrogen, (ii) a diamine of general formula $NH_2—(CH_2)_n—NH_2$, n=1 to 12 carbon atoms, (iii) a triamine of general formula $NH_2—(CH_2)_n—NH—(CH_2)_m—NH_2$, n=1 to 12 carbon atoms, m=1 to 12 carbon atoms, (iv) a linear or branched amino alcohol with 2 to 20 carbon atoms, (v) a linear or branched amino ester with 2 to 20 carbon atoms, (vi) a linear or branched amino amide with 2 to 20 carbon atoms, (vii) an amino acid or esters or amides thereof, (viii) a beta or gamma amino acid or its esters or amides, (ix) a peptide, optionally cyclic, comprising 2 to 30 amino acids, (x) a hydrazine monosubstituted with an aryl having 1, 2 or 3 aromatic rings, or a linear or branched alkyl with 1 to 12 carbon atoms, (xi) a glucamine optionally N-substituted with an alkyl group with 1 to 20 carbon atoms, (xii) a glucosamine optionally N-substituted with an alkyl group with 1 to 20 carbon atoms, (xiii) a pseudopeptide of general formula $H—(NH—CH(R)—CH_2—X—CO)_n—NHR''$, with R being a side chain of one of the 20 proteinogenic amino acids; X being independently, throughout the sequence, $CH_2$, O or NH; n=1-15; R''=H, or a short alkyl or aralkyl chain, (xiv) a pseudopeptide of general formula $R_a—CO—CH(R_b)—NH—CO—NH—CH(R_c)—CO—R_d$ in which $R_a$ and $R_d$ represent, independently of one another, H, a linear or branched C1-C6 alkyl group, a C3-C7 monocyclic cycloalkyl group, or a carboxylic acid protective group; $R_b$ represents the side chain of lysine, the amine of said side chain being optionally substituted with a group $—CO—(CH_2)_5—NH_2$; $R_c$ represents a side chain of one of the 20 proteinogenic amino acids, optionally protected by an ad hoc protective group, or (xv) a polymer represented by the general formula $NH_2—(CH_2(CH_2)_iNH)_{(n-1)}—H$, in which i=1, 2 or 3, n=1 to 1000, said polymer forming m coordination bonds with m platinum atoms, one of said coordination bonds being formed between Pt and $L_2$ of formula (II) and m-1 coordination bonds being formed with m-1 groups of formula 1:

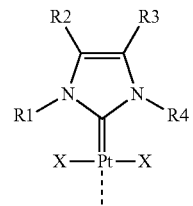

where $R_1$, $R_2$, $R_3$, $R_4$ and X are as defined above,
the number m being between 1 and n, the ratio m/n representing the number of platinum atoms to the number of amines of type —NH— or $—NH_2$,
and X represents iodine, bromine or chlorine;

(B) R1 or R4 represents:
a linear or branched C1-C6 alkyl group, substituted with a trimethylsilyl group, or a linear or branched, non-cyclized C7-C12 alkyl group, optionally substituted with an alkoxy group with 1 to 12 carbon atoms, with a $CF_3$ group or with a trimethylsilyl group,
a linear or branched C2-C12 alkenyl group, substituted with a trimethylsilyl group,
a linear or branched C2-C12 alkynyl group, optionally substituted with an alkyl group with 1 to 12 carbon atoms, with an alkoxy group with 1 to 12 carbon atoms, with a $CF_3$ group or with a trimethylsilyl group,
a polymer represented by the formula $—(CH_2CH_2O)_n—R'$ or a polymer represented by the formula $—(CH_2CH_2CH_2O)_n—R'$, in which n=1 to 40, and R' is a C1-C12 alkyl group, or (C) R2 or R3 represents:
an aralkyl group with a C1-C12 carbon chain, the aralkyl group being optionally substituted with a C1-C12 alkyl group, or with a C1-C12 alkoxy group, with a $CF_3$ group, or with a trimethylsilyl group, or
a linear or branched C2-C12 alkynyl, optionally substituted with an alkyl group with 1 to 12 carbon atoms, with an alkoxy group with 1 to 12 carbon atoms, with a $CF_3$ group, or with a trimethylsilyl group.

16. The process according to claim 2, comprising adding a base selected from triethylamine, or diisopropylethylamine, when the ligand $L_2$ is in the form of salt.

17. The process according to claim 3, comprising adding a base selected from triethylamine, or diisopropylethylamine, when the ligand $L_2$ is in the form of salt.

18. The process according to claim 2, wherein said compound of formula I is reacted with a salt of a ligand $L_2$, said salt being in the form of ammonium hydrochloride or ammonium trifluoroacetate.

19. The process according to claim 3, wherein said compound of formula I is reacted with a salt of a ligand $L_2$, said salt being in the form of ammonium hydrochloride or ammonium trifluoroacetate, to obtain a compound of formula (II) wherein $L_2$ is an amine.

20. The process according to claim 4, wherein said compound of formula I is reacted with a salt of a ligand $L_2$, said salt being in the form of ammonium hydrochloride or ammonium trifluoroacetate, to obtain a compound of formula (II) wherein $L_2$ is an amine.

* * * * *